US012582845B2

(12) United States Patent
Bassalow et al.

(10) Patent No.: US 12,582,845 B2
(45) Date of Patent: Mar. 24, 2026

(54) METHODS FOR TUMOR TRACKING

(71) Applicant: RefleXion Medical, Inc., Hayward, CA (US)

(72) Inventors: Rostem Bassalow, Lacey, WA (US); George Andrew Zdasiuk, Portola Valley, CA (US)

(73) Assignee: RefleXion Medical, Inc., Hayward, CA (US)

( * ) Notice: Subject to any disclaimer, the term of this patent is extended or adjusted under 35 U.S.C. 154(b) by 479 days.

(21) Appl. No.: 18/311,069

(22) Filed: May 2, 2023

(65) Prior Publication Data

US 2023/0285777 A1     Sep. 14, 2023

Related U.S. Application Data

(63) Continuation of application No. PCT/US2021/057948, filed on Nov. 3, 2021.

(60) Provisional application No. 63/109,742, filed on Nov. 4, 2020.

(51) Int. Cl.
*A61N 5/10*         (2006.01)
*A61B 6/03*         (2006.01)

(52) U.S. Cl.
CPC ............ *A61N 5/1049* (2013.01); *A61B 6/037* (2013.01); *A61N 2005/1051* (2013.01); *A61N 2005/1052* (2013.01); *A61N 2005/1059* (2013.01)

(58) Field of Classification Search
None
See application file for complete search history.

(56) References Cited

U.S. PATENT DOCUMENTS

| | | | |
|---|---|---|---|
| 3,794,840 A | 2/1974 | Scott | |
| 5,015,851 A | 5/1991 | Singh et al. | |
| 5,394,452 A | 2/1995 | Swerdloff et al. | |
| 5,548,627 A | 8/1996 | Swerdloff et al. | |
| 5,661,773 A | 8/1997 | Swerdloff et al. | |
| 5,724,400 A | 3/1998 | Swerdloff et al. | |
| 5,813,985 A | 9/1998 | Carroll | |

(Continued)

FOREIGN PATENT DOCUMENTS

| | | |
|---|---|---|
| CA | 1121072 A | 3/1982 |
| CN | 1681436 A | 10/2005 |

(Continued)

OTHER PUBLICATIONS

Extended European Search Report mailed on Jun. 23, 2023, for EP Application No. 20 840 804.7, filed on Jul. 2, 2020, 7 pages.

(Continued)

*Primary Examiner* — Hoon K Song
(74) *Attorney, Agent, or Firm* — Cooley LLP

(57) ABSTRACT

Disclosed herein are methods for determining the location of a moving target region (e.g., a tumor) based on the location of the center of its range of motion and the location of a target region surrogate, during a radiotherapy treatment session or a quality assurance (QA) session. These methods comprise characterizing the motion range of the target region, calculating the location of the center of the motion range, and determining a correlation between the position of the target region surrogate and the displacement of the target region from the center of the motion range as the target region moves.

37 Claims, 10 Drawing Sheets

(56) References Cited

U.S. PATENT DOCUMENTS

| | | | |
|---|---|---|---|
| 6,438,202 B1 | 8/2002 | Olivera et al. |
| 6,455,856 B1 | 9/2002 | Gagnon |
| 6,504,899 B2 | 1/2003 | Pugachev et al. |
| 6,700,949 B2 | 3/2004 | Susami et al. |
| 6,735,277 B2 | 5/2004 | McNutt et al. |
| 6,888,919 B2 | 5/2005 | Graf |
| 7,020,233 B1 | 3/2006 | Tybinkowski et al. |
| 7,085,347 B2 | 8/2006 | Mihara et al. |
| 7,177,386 B2 | 2/2007 | Mostafavi et al. |
| 7,191,100 B2 | 3/2007 | Mostafavi |
| 7,263,165 B2 | 8/2007 | Ghelmansarai |
| 7,265,356 B2 | 9/2007 | Pelizzari et al. |
| 7,302,033 B2 | 11/2007 | Carrano et al. |
| 7,302,038 B2 | 11/2007 | Mackie et al. |
| 7,356,112 B2 | 4/2008 | Brown et al. |
| 7,367,955 B2 | 5/2008 | Zhang et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,522,779 B2 | 4/2009 | Fu et al. |
| 7,620,444 B2 | 11/2009 | Le et al. |
| 7,623,623 B2 | 11/2009 | Raanes et al. |
| 7,649,981 B2 | 1/2010 | Seppi et al. |
| 7,711,087 B2 | 5/2010 | Mostafavi |
| 7,715,606 B2 | 5/2010 | Jeung et al. |
| 7,769,430 B2 | 8/2010 | Mostafavi |
| 7,778,691 B2 | 8/2010 | Zhang et al. |
| 7,783,335 B2 | 8/2010 | Le Corre |
| 7,820,989 B2 | 10/2010 | Sommer |
| 7,831,073 B2 | 11/2010 | Fu et al. |
| 7,869,562 B2 | 1/2011 | Khamene et al. |
| 7,869,862 B2 | 1/2011 | Seppi et al. |
| 7,885,371 B2 | 2/2011 | Thibault et al. |
| 7,906,770 B2 | 3/2011 | Otto |
| 7,945,021 B2 | 5/2011 | Shapiro et al. |
| 7,983,380 B2 | 7/2011 | Guertin et al. |
| 8,017,915 B2 | 9/2011 | Mazin |
| 8,060,177 B2 | 11/2011 | Hamill |
| 8,086,004 B2 | 12/2011 | Kuduvalli et al. |
| 8,093,568 B2 | 1/2012 | Mackie et al. |
| 8,148,703 B2 | 4/2012 | Sommer |
| 8,160,205 B2 | 4/2012 | Saracen et al. |
| 8,193,508 B2 | 6/2012 | Shchory et al. |
| 8,295,430 B2 | 10/2012 | Zhu et al. |
| 8,295,435 B2 | 10/2012 | Wang et al. |
| 8,295,906 B2 | 10/2012 | Saunders et al. |
| 8,303,505 B2 | 11/2012 | Webler et al. |
| 8,311,185 B2 | 11/2012 | Seppi et al. |
| 8,331,532 B2 | 12/2012 | Nord et al. |
| 8,457,372 B2 | 6/2013 | Fu et al. |
| 8,461,538 B2 | 6/2013 | Mazin |
| 8,509,383 B2 | 8/2013 | Lu et al. |
| 8,536,547 B2 | 9/2013 | Maurer, Jr. et al. |
| 8,559,596 B2 | 10/2013 | Thomson et al. |
| 8,571,639 B2 | 10/2013 | Mostafavi |
| 8,588,367 B2 | 11/2013 | Busch et al. |
| 8,594,769 B2 | 11/2013 | Mostafavi |
| 8,606,349 B2 | 12/2013 | Rousso et al. |
| 8,641,592 B2 | 2/2014 | Yu |
| 8,745,789 B2 | 6/2014 | Saracen et al. |
| 8,748,825 B2 | 6/2014 | Mazin |
| 8,767,917 B2 | 7/2014 | Ruchala et al. |
| 8,788,020 B2 | 7/2014 | Mostafavi et al. |
| 8,824,630 B2 | 9/2014 | Maurer, Jr. et al. |
| 8,831,706 B2 | 9/2014 | Fu et al. |
| 8,861,672 B2 | 10/2014 | Maltz et al. |
| 8,874,187 B2 | 10/2014 | Thomson et al. |
| 8,917,813 B2 | 12/2014 | Maurer, Jr. |
| 9,155,909 B2 | 10/2015 | Ishikawa |
| 9,205,281 B2 | 12/2015 | Mazin |
| 9,232,928 B2 | 1/2016 | Mostafavi |
| 9,248,312 B2 | 2/2016 | Li et al. |
| 9,283,403 B2 | 3/2016 | Mazin et al. |
| 9,446,264 B2 | 9/2016 | Sawkey et al. |
| 9,616,251 B2 | 4/2017 | Filiberti et al. |
| 9,623,262 B2 | 4/2017 | Vaziri et al. |
| 9,649,509 B2 | 5/2017 | Mazin et al. |
| 9,694,208 B2 | 7/2017 | Mazin et al. |
| 9,731,148 B2 | 8/2017 | Olivera et al. |
| 9,764,161 B2 | 9/2017 | Mazin et al. |
| 9,820,700 B2 | 11/2017 | Mazin |
| 9,849,308 B2 | 12/2017 | Berlinger et al. |
| 9,895,554 B2 | 2/2018 | Nguyen |
| 9,990,711 B2 | 6/2018 | Lugosi et al. |
| 10,065,049 B2 | 9/2018 | Lugosi et al. |
| 10,143,857 B2 | 12/2018 | Mazin et al. |
| 10,159,852 B2 | 12/2018 | Mazin et al. |
| 10,166,405 B2 | 1/2019 | Nguyen |
| 10,279,196 B2 | 5/2019 | West et al. |
| 10,327,716 B2 | 6/2019 | Mazin |
| 10,449,389 B2 | 10/2019 | Ollila et al. |
| 10,456,600 B2 | 10/2019 | Owens et al. |
| 10,617,890 B2 | 4/2020 | Mazin et al. |
| 10,646,188 B2 | 5/2020 | Mostafavi et al. |
| 10,688,320 B2 | 6/2020 | Voronenko et al. |
| 10,695,583 B2 | 6/2020 | Mazin et al. |
| 10,695,586 B2 | 6/2020 | Harper et al. |
| 10,702,715 B2 | 7/2020 | Pearce et al. |
| 10,737,118 B2 | 8/2020 | Mostafavi |
| 10,745,253 B2 | 8/2020 | Saracen et al. |
| 10,799,716 B2 | 10/2020 | Morgas et al. |
| 10,806,368 B2 | 10/2020 | Hebert |
| 10,806,947 B2 | 10/2020 | Foo et al. |
| 10,835,761 B2 | 11/2020 | Beriault et al. |
| 10,918,885 B2 | 2/2021 | Haas et al. |
| 10,946,215 B2 | 3/2021 | Sjolund |
| 10,959,686 B2 | 3/2021 | Mazin |
| 10,960,230 B2 | 3/2021 | Nguyen |
| 11,033,757 B2 | 6/2021 | Voronenko et al. |
| 11,083,913 B2 | 8/2021 | Lachaine et al. |
| 11,141,607 B2 | 10/2021 | Mazin et al. |
| 11,154,269 B2 | 10/2021 | Shea et al. |
| 11,173,324 B2 | 11/2021 | Paysan et al. |
| 11,278,737 B2 | 3/2022 | Peltola et al. |
| 11,291,858 B2 | 4/2022 | MacDonald et al. |
| 11,309,072 B2 | 4/2022 | Carmi |
| 11,358,008 B2 | 6/2022 | Voronenko et al. |
| 11,369,805 B2 | 6/2022 | Maltz |
| 11,369,806 B2 | 6/2022 | Laurence, Jr. et al. |
| 11,406,846 B2 | 8/2022 | Voronenko et al. |
| 11,478,662 B2 | 10/2022 | Sayeh et al. |
| 11,504,548 B2 | 11/2022 | Fong de los Santos et al. |
| 11,504,550 B2 | 11/2022 | Maolinbay |
| 11,520,415 B2 | 12/2022 | Douglas et al. |
| 11,596,807 B2 | 3/2023 | Maurer et al. |
| 11,617,903 B2 | 4/2023 | Lamb et al. |
| 11,627,920 B2 | 4/2023 | Mazin |
| 11,633,626 B2 | 4/2023 | Voronenko et al. |
| 11,642,027 B2 | 5/2023 | Otto |
| 11,684,801 B2 | 6/2023 | Schadewaldit et al. |
| 11,896,848 B2 | 2/2024 | Janardhanan et al. |
| 12,002,216 B2 | 6/2024 | Albrecht et al. |
| 12,115,386 B2 | 10/2024 | Voronenko et al. |
| 12,167,922 B2 | 12/2024 | Mazin |
| 12,214,218 B2 | 2/2025 | Kolesnick et al. |
| 12,251,579 B2 | 3/2025 | Voronenko |
| 12,303,718 B2 | 5/2025 | Owens et al. |
| 2002/0051513 A1 | 5/2002 | Pugachev et al. |
| 2002/0163994 A1 | 11/2002 | Jones |
| 2002/0191734 A1 | 12/2002 | Kojima et al. |
| 2003/0036700 A1 | 2/2003 | Weinberg |
| 2003/0058984 A1 | 3/2003 | Susami et al. |
| 2003/0128801 A1 | 7/2003 | Eisenberg et al. |
| 2003/0219098 A1 | 11/2003 | McNutt et al. |
| 2003/0235531 A1 | 12/2003 | Adair |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057557 A1 | 3/2004 | Nafstadius |
| 2004/0116804 A1 | 6/2004 | Mostafavi |
| 2004/0162457 A1 | 8/2004 | Maggiore et al. |
| 2004/0218719 A1 | 11/2004 | Brown et al. |
| 2005/0201509 A1 | 9/2005 | Mostafavi et al. |
| 2005/0201510 A1 | 9/2005 | Mostafavi |

(56) References Cited

U.S. PATENT DOCUMENTS

| | | |
|---|---|---|
| 2005/0207531 A1 | 9/2005 | Dempsey et al. |
| 2005/0213705 A1 | 9/2005 | Hoffman |
| 2005/0228255 A1 | 10/2005 | Saracen et al. |
| 2005/0234327 A1 | 10/2005 | Saracen et al. |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0159220 A1 | 7/2006 | Heuscher |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0025496 A1 | 2/2007 | Brown et al. |
| 2007/0025513 A1 | 2/2007 | Ghelmansarai |
| 2007/0025524 A1 | 2/2007 | Yue |
| 2007/0053491 A1 | 3/2007 | Schildkraut et al. |
| 2007/0085012 A1 | 4/2007 | Thompson |
| 2007/0133749 A1 | 6/2007 | Mazin et al. |
| 2007/0153969 A1 | 7/2007 | Maschke |
| 2007/0165779 A1 | 7/2007 | Chen et al. |
| 2007/0167801 A1 | 7/2007 | Webler et al. |
| 2007/0237290 A1 | 10/2007 | Mostafavi |
| 2007/0265230 A1 | 11/2007 | Rousso et al. |
| 2007/0265528 A1 | 11/2007 | Xu et al. |
| 2008/0002811 A1 | 1/2008 | Allison |
| 2008/0031404 A1 | 2/2008 | Khamene et al. |
| 2008/0071131 A1 | 3/2008 | Rietzel |
| 2008/0095416 A1 | 4/2008 | Jeung et al. |
| 2008/0128631 A1 | 6/2008 | Suhami |
| 2008/0156993 A1 | 7/2008 | Weinberg et al. |
| 2008/0177179 A1 | 7/2008 | Stubbs et al. |
| 2008/0205588 A1 | 8/2008 | Kim |
| 2008/0230705 A1 | 9/2008 | Rousso et al. |
| 2008/0273659 A1 | 11/2008 | Guertin et al. |
| 2009/0003655 A1 | 1/2009 | Wollenweber |
| 2009/0052623 A1 | 2/2009 | Tome et al. |
| 2009/0088622 A1 | 4/2009 | Mostafavi |
| 2009/0116616 A1 | 5/2009 | Lu et al. |
| 2009/0169082 A1 | 7/2009 | Mizuta et al. |
| 2009/0252291 A1 | 10/2009 | Lu et al. |
| 2009/0256078 A1 | 10/2009 | Mazin |
| 2009/0309046 A1 | 12/2009 | Balakin |
| 2010/0040197 A1 | 2/2010 | Maniawski et al. |
| 2010/0049030 A1 | 2/2010 | Saunders et al. |
| 2010/0054411 A1 | 3/2010 | Nord et al. |
| 2010/0067660 A1 | 3/2010 | Maurer, Jr. et al. |
| 2010/0074400 A1 | 3/2010 | Sendai |
| 2010/0074408 A1 | 3/2010 | Bert et al. |
| 2010/0074498 A1 | 3/2010 | Breeding et al. |
| 2010/0088339 A1* | 4/2010 | Rietzel .................. A61N 5/103 |
| | | 707/E17.014 |
| 2010/0150309 A1 | 6/2010 | Nord et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0258138 A1 | 10/2010 | Sorensen et al. |
| 2010/0266099 A1 | 10/2010 | Busch et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0122997 A1 | 5/2011 | Lu et al. |
| 2011/0215248 A1 | 9/2011 | Lewellen et al. |
| 2011/0291015 A1 | 12/2011 | Mazin |
| 2011/0297833 A1 | 12/2011 | Takayama |
| 2011/0309252 A1 | 12/2011 | Moriyasu et al. |
| 2011/0313232 A1 | 12/2011 | Balakin |
| 2012/0004518 A1 | 1/2012 | D'Souza et al. |
| 2012/0053961 A1 | 3/2012 | Wang et al. |
| 2012/0161014 A1 | 6/2012 | Yamaya et al. |
| 2012/0174317 A1 | 7/2012 | Saracen et al. |
| 2012/0189102 A1 | 7/2012 | Maurer, Jr. et al. |
| 2012/0320055 A1 | 12/2012 | Pekar et al. |
| 2013/0018232 A1 | 1/2013 | D'Souza et al. |
| 2013/0025055 A1 | 1/2013 | Saracen et al. |
| 2013/0060134 A1 | 3/2013 | Eshima et al. |
| 2013/0083004 A1 | 4/2013 | Nord et al. |
| 2013/0188856 A1 | 7/2013 | Adler, Jr. et al. |
| 2013/0197878 A1 | 8/2013 | Fiege et al. |
| 2013/0279658 A1 | 10/2013 | Mazin |
| 2013/0303898 A1 | 11/2013 | Kinahan et al. |
| 2014/0107460 A1 | 4/2014 | Nguyen |
| 2014/0126700 A1 | 5/2014 | Gertner et al. |
| 2014/0163368 A1 | 6/2014 | Rousso et al. |
| 2014/0193336 A1 | 7/2014 | Rousso et al. |
| 2014/0217294 A1 | 8/2014 | Rothfuss et al. |
| 2014/0228613 A1 | 8/2014 | Mazin et al. |
| 2014/0257096 A1 | 9/2014 | Prevrhal et al. |
| 2014/0275962 A1 | 9/2014 | Foo et al. |
| 2014/0371581 A1 | 12/2014 | Mostafavi et al. |
| 2015/0043709 A1 | 2/2015 | Shapiro et al. |
| 2015/0055849 A1 | 2/2015 | Galavis et al. |
| 2015/0087960 A1 | 3/2015 | Treffert |
| 2015/0094519 A1 | 4/2015 | Kuusela et al. |
| 2015/0355347 A1 | 12/2015 | Pratx |
| 2015/0360056 A1 | 12/2015 | Xing et al. |
| 2016/0023019 A1 | 1/2016 | Filiberti et al. |
| 2016/0038767 A1 | 2/2016 | Wiersma et al. |
| 2016/0296766 A1 | 10/2016 | El Fakhri et al. |
| 2016/0361566 A1 | 12/2016 | Larkin et al. |
| 2017/0007447 A1 | 1/2017 | Goldshleger et al. |
| 2017/0023494 A1 | 1/2017 | Yu et al. |
| 2017/0087385 A1 | 3/2017 | Miettinen et al. |
| 2017/0209715 A1 | 7/2017 | Ruebel et al. |
| 2018/0133518 A1 | 5/2018 | Harper et al. |
| 2018/0154179 A1 | 6/2018 | Ollila et al. |
| 2018/0345042 A1 | 12/2018 | Voronenko et al. |
| 2018/0369611 A1 | 12/2018 | Owens et al. |
| 2019/0001152 A1 | 1/2019 | O'Connor et al. |
| 2019/0054315 A1 | 2/2019 | Isola et al. |
| 2019/0054320 A1 | 2/2019 | Owens et al. |
| 2019/0070436 A1 | 3/2019 | Willcut et al. |
| 2019/0130569 A1 | 5/2019 | Liu et al. |
| 2019/0217123 A1 | 7/2019 | West et al. |
| 2019/0262630 A1 | 8/2019 | Voronenko et al. |
| 2019/0279094 A1 | 9/2019 | Baughman et al. |
| 2019/0357859 A1 | 11/2019 | Mazin |
| 2019/0381338 A1 | 12/2019 | Voronenko et al. |
| 2020/0016432 A1 | 1/2020 | Maolinbay |
| 2020/0206536 A1 | 7/2020 | Wang et al. |
| 2021/0327560 A1 | 10/2021 | Carmi |
| 2021/0339047 A1 | 11/2021 | Janardhanan et al. |
| 2022/0096867 A1 | 3/2022 | Mazin et al. |
| 2022/0126117 A1 | 4/2022 | Voronenko et al. |
| 2022/0218204 A1 | 7/2022 | Adler, Jr. et al. |
| 2022/0395707 A1 | 12/2022 | Laurence, Jr. et al. |
| 2023/0038498 A1* | 2/2023 | Xu ...................... A61B 34/30 |
| 2023/0067048 A1 | 3/2023 | Voronenko et al. |
| 2023/0230253 A1 | 7/2023 | Albrecht et al. |
| 2023/0256266 A1 | 8/2023 | Voronenko |
| 2023/0356003 A1 | 11/2023 | Voronenko et al. |
| 2024/0104767 A1 | 3/2024 | Voronenko et al. |
| 2024/0180497 A1* | 6/2024 | Xia ...................... A61B 5/0044 |
| 2024/0189624 A1 | 6/2024 | Olcott et al. |
| 2024/0316363 A1 | 9/2024 | Voronenko et al. |
| 2024/0354946 A1 | 10/2024 | Shi et al. |
| 2025/0032818 A1 | 1/2025 | Voronenko et al. |
| 2025/0121211 A1 | 4/2025 | Mazin et al. |
| 2025/0204872 A1 | 6/2025 | Mazin |
| 2025/0288828 A1 | 9/2025 | Voronenko |

FOREIGN PATENT DOCUMENTS

| | | |
|---|---|---|
| CN | 1824342 A | 8/2006 |
| CN | 1960780 A | 5/2007 |
| CN | 101013095 A | 8/2007 |
| CN | 101305297 A | 11/2008 |
| CN | 101970043 A | 2/2011 |
| CN | 103180014 A | 6/2013 |
| CN | 104284697 A | 1/2015 |
| CN | 105658279 A | 6/2016 |
| CN | 106563211 A | 4/2017 |

(56)                References Cited

FOREIGN PATENT DOCUMENTS

| | | | |
|---|---|---|---|
| CN | 107072595 A | | 8/2017 |
| CN | 107072628 A | | 8/2017 |
| DE | 10 2008 053321 A1 | | 5/2010 |
| EP | 3 565 471 B1 | | 11/2022 |
| JP | 09-33658 A | | 2/1997 |
| JP | 09-189769 A2 | | 7/1997 |
| JP | H-11-290466 A | | 10/1999 |
| JP | 2000-105279 A | | 4/2000 |
| JP | 2001-340474 A | | 12/2001 |
| JP | 2003-117010 A | | 4/2003 |
| JP | 2003-534823 A | | 11/2003 |
| JP | 2004-073404 A | | 3/2004 |
| JP | 2004-513735 A | | 5/2004 |
| JP | 2005-261941 A | | 9/2005 |
| JP | 2006-145281 A | | 6/2006 |
| JP | 2007-502166 A | | 2/2007 |
| JP | 2007-507246 A | | 3/2007 |
| JP | 2009-005440 A | | 1/2009 |
| JP | 2009-544101 A | | 12/2009 |
| JP | 2010-517655 A | | 5/2010 |
| JP | 2011-514213 A | | 5/2011 |
| JP | 2012-506734 A | | 3/2012 |
| JP | 6210972 B2 | | 10/2017 |
| JP | 2017-199876 A | | 11/2017 |
| JP | 6571816 B2 | | 9/2019 |
| JP | 2020-522307 A | | 7/2020 |
| JP | 6796886 B2 | | 12/2020 |
| JP | 7274773 B2 | | 5/2023 |
| WO | WO-2005/110495 A1 | | 11/2005 |
| WO | WO-2006/051531 A2 | | 5/2006 |
| WO | WO-2006/086765 A2 | | 8/2006 |
| WO | WO-2007/120674 A2 | | 10/2007 |
| WO | WO-2008/024463 A2 | | 2/2008 |
| WO | WO-2008/024463 A3 | | 2/2008 |
| WO | WO-2008/127368 A2 | | 10/2008 |
| WO | WO-2009/111580 A2 | | 9/2009 |
| WO | WO-2009/111580 A3 | | 9/2009 |
| WO | WO-2009/114117 A2 | | 9/2009 |
| WO | WO-2010/015358 A1 | | 2/2010 |
| WO | WO-2010/018477 A2 | | 2/2010 |
| WO | WO-2010/018477 A3 | | 2/2010 |
| WO | WO-2010/110255 A1 | | 9/2010 |
| WO | WO-2016/023786 A1 | | 2/2016 |
| WO | WO-2016/064750 A1 | | 4/2016 |
| WO | WO-2018/024487 A1 | | 2/2018 |
| WO | WO-2018/090091 A1 | | 5/2018 |
| WO | WO-2018/183748 A1 | | 10/2018 |
| WO | WO-2018/222751 A1 | | 12/2018 |
| WO | WO 2020/141021 A1 * | | 3/2019 |
| WO | WO-2019/160958 A1 | | 8/2019 |
| WO | WO-2020/144134 A1 | | 7/2020 |
| WO | WO-2021/011207 A1 | | 1/2021 |
| WO | WO-2022/031750 A1 | | 2/2022 |
| WO | WO-2022/098794 A1 | | 5/2022 |
| WO | WO-2022/182681 A2 | | 9/2022 |
| WO | WO-2022/182681 A3 | | 9/2022 |
| WO | WO-2023/070088 A1 | | 4/2023 |
| WO | WO-2024/107734 A1 | | 5/2024 |
| WO | WO-2024/206384 A1 | | 10/2024 |

OTHER PUBLICATIONS

Final Office Action mailed on Aug. 21, 2023, for U.S. Appl. No. 17/485,059, filed Sep. 24, 2021, 10 pages.

Bao, Q. et al. (2010). "Estimation of the minimum detectable activity of preclinical PET imaging systems with an analytical method," Med. Phys. 37:6070-6083.

Black, Q.C. et al. (2004). "Defining a Radiotherapy Target with positron emission tomography," Int. J. Radiation Oncology Biol. Phys. 60:1272-1282.

Bush, S. (Sep. 2020). "Add noise for clearer signals," located at https://www.electronicsweekly.com/news/research-news/add-noise-clearer-signals-2020-09/, 4 total pages.

Corrected Notice of Allowability mailed on Feb. 3, 2021, for U.S. Appl. No. 16/425,416, filed May 29, 2019, 2 pages.

Corrected Notice of Allowability mailed on Mar. 13, 2023, for U.S. Appl. No. 17/235,812, filed Apr. 20, 2021, 4 pages.

Corrected Notice of Allowability mailed on Mar. 16, 2023, for U.S. Appl. No. 17/203,532, filed Mar. 16, 2021, 2 pages.

Erdi, Y.E. (2007). "The use of PET for radiotherapy," Curr. Medical Imaging Reviews 3(1):3-16.

Extended European Search Report mailed on Mar. 31, 2017, for European Application No. 09 719 473.2, filed on Mar. 9, 2009, 8 pages.

Extended European Search Report mailed on Oct. 7, 2015, for European Application No. 12 763 280.0, filed on Mar. 30, 2012, 11 pages.

Extended European Search Report mailed on Nov. 21, 2018, for European Application No. 18 168 947.2, filed on Mar. 30, 2012, 8 pages.

Extended European Search Report mailed on Oct. 30, 2020, for EP Application No. 20 179 036.7, filed on Mar. 9, 2009, 12 pages.

Extended European Search Report mailed on Feb. 3, 2021, for EP Application No. 18 810 297.4, filed on May 30, 2018, 4 pages.

Final Office Action mailed on Aug. 15, 2012, for U.S. Appl. No. 13/209,275, filed Aug. 12, 2011, 8 pages.

Final Office Action mailed on Aug. 2, 2018, for U.S. Appl. No. 15/684,710, filed Aug. 23, 2017, 8 pages.

Internal Atomic Energy Agency (Oct. 2008). "The Role of PET/CT in Radiation Treatment Planning for Cancer Patient Treatment," located at https://www-pub.iaea.org/MTCD/Publications/PDF/te_1603_web.pdf, 40 total pages.

International Search Report mailed on May 4, 2009, for PCT Application No. PCT/US2009/01500, filed on Mar. 9, 2009, 3 pages.

International Search Report mailed on Jul. 20, 2012, for PCT Patent Application No. PCT/US2012/31704, filed on Mar. 30, 2012, 2 pages.

International Search Report mailed on Jan. 17, 2018, for PCT Application No. PCT/US2017/061728, filed on Nov. 15, 2017, 2 pages.

International Search Report mailed on Oct. 3, 2018, for PCT Application No. PCT/US2018/035188, filed on May 30, 2018, 4 pages.

International Search Report mailed on Apr. 23, 2020, for PCT Application No. PCT/US2020/013927, filed on Jan. 16, 2020, 3 pages.

International Search Report mailed on Dec. 1, 2020, for PCT Application No. PCT/US2020/040774, filed on Jul. 2, 2020, 4 pages.

International Search Report mailed on Mar. 10, 2022, for PCT Application No. PCT/US2021/057948, filed on Nov. 3, 2021, 4 pages.

International Search Report mailed on Dec. 16, 2021, for PCT Application No. PCT/US2021/044405, filed on Aug. 3, 2021, 4 pages.

International Search Report mailed on Aug. 24, 2022, for PCT Application No. PCT/US2022/017375, filed on Feb. 22, 2022, 7 pages.

International Search Report mailed on Apr. 5, 2023, for PCT Application No. PCT/US2022/078511, filed on Oct. 21, 2022, 6 pages.

Non-Final Office Action mailed on Feb. 24, 2017, for U.S. Appl. No. 15/069,390, filed Mar. 14, 2016, 6 pages.

Non-Final Office Action mailed on Feb. 21, 2018, for U.S. Appl. No. 15/684,710, filed Aug. 23, 2017, 10 pages.

Non-Final Office Action mailed on Mar. 27, 2018, for U.S. Appl. No. 15/684,693, filed Aug. 23, 2017, 7 pages.

Non-Final Office Action mailed on Aug. 30, 2019, for U.S. Appl. No. 16/193,725, filed Nov. 16, 2018, 5 pages.

Non-Final Office Action mailed on Sep. 19, 2019, for U.S. Appl. No. 16/217,417, filed Dec. 12, 2018, 7 pages.

Non-Final Office Action mailed on Dec. 6, 2019, for U.S. Appl. No. 15/993,325, filed May 30, 2018, 8 pages.

Non-Final Office Action mailed on Oct. 29, 2020, for U.S. Appl. No. 16/834,956, filed Mar. 30, 2020, 7 pages.

(56)     References Cited

OTHER PUBLICATIONS

Non-Final Office Action mailed on Dec. 22, 2020, for U.S. Appl. No. 16/554,258, filed Aug. 28, 2019, 11 pages.

Non-Final Office Action mailed on Dec. 21, 2021, for U.S. Appl. No. 16/412,780, filed May 15, 2019, 15 pages.

Non-Final Office Action mailed on Jul. 5, 2022, for U.S. Appl. No. 17/203,532, filed Mar. 16, 2021, 13 pages.

Non-Final Office Action mailed on Aug. 30, 2022, for U.S. Appl. No. 17/235,812, filed Apr. 20, 2021, 8 pages.

Non-Final Office Action mailed on Jan. 27, 2023, for U.S. Appl. No. 17/485,059, filed Sep. 24, 2021, 11 pages.

Notice of Allowance mailed on Jul. 25, 2011, for U.S. Appl. No. 12/367,679, filed Feb. 9, 2009, 7 pages.

Notice of Allowance mailed on Apr. 9, 2014, for U.S. Appl. No. 13/895,255, filed May 15, 2013, 7 pages.

Notice of Allowance mailed on Oct. 27, 2015, for U.S. Appl. No. 14/278,973, filed May 15, 2014, 8 pages.

Notice of Allowance mailed on Mar. 27, 2013, for U.S. Appl. No. 13/209,275, filed Aug. 12, 2011, 9 pages.

Notice of Allowance mailed on Oct. 5, 2017, for U.S. Appl. No. 14/951,194, filed Nov. 24, 2015, 11 pages.

Notice of Allowance mailed on May 18, 2017, for U.S. Appl. No. 15/069,390, filed Mar. 14, 2016, 5 pages.

Notice of Allowance mailed on Jul. 19, 2017, for U.S. Appl. No. 15/499,671, filed Apr. 27, 2017, 8 pages.

Notice of Allowance mailed on Oct. 3, 2018, for U.S. Appl. No. 15/684,693, filed Aug. 23, 2017, 5 pages.

Notice of Allowance mailed on Oct. 25, 2018, for U.S. Appl. No. 15/684,710, filed Aug. 23, 2017, 7 pages.

Notice of Allowance mailed on Apr. 4, 2019, for U.S. Appl. No. 15/807,383, filed Nov. 8, 2017, 11 pages.

Notice of Allowance mailed on Jan. 21, 2020, for U.S. Appl. No. 16/193,725, filed Nov. 16, 2018, 7 pages.

Notice of Allowance mailed on Mar. 13, 2020, for U.S. Appl. No. 16/217,417, filed Dec. 12, 2018, 6 pages.

Notice of Allowance mailed on Apr. 20, 2020, for U.S. Appl. No. 15/993,325, filed May 30, 2018, 7 pages.

Notice of Allowance mailed on Jan. 12, 2021, for U.S. Appl. No. 16/425,416, filed Jon May 29, 2019, 13 pages.

Notice of Allowance mailed on Jun. 21, 2021, for U.S. Appl. No. 16/834,956, filed Mar. 30, 2020, 7 pages.

Notice of Allowance mailed on Jun. 8, 2022, for U.S. Appl. No. 16/412,780, filed May 15, 2019, 8 pages.

Notice of Allowance mailed on Dec. 15, 2022, for U.S. Appl. No. 17/203,532, filed Mar. 16, 2021, 8 pages.

Notice of Allowance mailed on Feb. 1, 2023, for U.S. Appl. No. 17/235,812, filed Apr. 20, 2021, 7 pages.

Persson, G.F. et al. (Sep. 2013). "Stability of percutaneously implanted markers for lung stereotactic radiotherapy," J. Appl. Clin. Med. Phys. 14:187-195.

Shirvani, S.M. et al. (Jan. 2021). "Biology-guided radiotherapy: redefining the role of radiotherapy in metastatic cancer," Br. J. Radiol. 94:20200873, 10 total pages.

Wang, D. et al. (2006). "Initial experience of FDG-PET/CT guided IMRT of head-and-neck carcinoma," Int. J. Radiation Oncology Biol. Phys. 65:143-151.

Written Opinion of the International Searching Authority mailed on May 4, 2009, for PCT Application No. PCT/US2009/01500, filed on Mar. 9, 2009, 5 pages.

Written Opinion mailed on Jul. 20, 2012, for PCT Patent Application No. PCT/US2012/31704, filed on Mar. 30, 2012, 10 pages.

Written Opinion of the International Searching Authority mailed on Jan. 17, 2018, for PCT Application No. PCT/US2017/061728, filed on Nov. 15, 2017, 7 pages.

Written Opinion of the International Searching Authority mailed on Oct. 3, 2018, for PCT Application No. PCT/US2018/035188, filed on May 30, 2018, 28 pages.

Written Opinion of the International Searching Authority mailed on Apr. 23, 2020, for PCT Application No. PCT/US2020/013927, filed on Jan. 16, 2020, 4 pages.

Written Opinion of the International Searching Authority mailed on Dec. 1, 2020, for PCT Application No. PCT/US2020/040774, filed on Jul. 2, 2020, 8 pages.

Written Opinion of the International Searching Authority mailed on Mar. 10, 2022, for PCT Application No. PCT/US2021/057948, filed on Nov. 7, 2021, 7 pages.

Written Opinion of the International Searching Authority mailed on Dec. 16, 2021, for PCT Application No. PCT/US2021/044405, filed on Aug. 3, 2021, 5 pages.

Written Opinion of the International Searching Authority mailed on Aug. 24, 2022, for PCT Application No. PCT/US2022/017375, filed on Feb. 22, 2022, 11 pages.

Written Opinion of the International Searching Authority mailed on Apr. 5, 2023, for PCT Application No. PCT/US2022/078511, filed on Oct. 21, 2022, 6 pages.

Chetty, I.J. et al. (Apr. 2004). "Accounting for center-of-mass target motion using convolution methods in Monte Carlo-based dose calculations of the lung," Med. Phys. 31(4): 925-932.

EP Application No. 23 160 060.2, Extended European Search Report mailed Jan. 24, 2024, Applicant RefleXion Medical, Inc., 12 pages.

EP Application No. 21 853 184.6, Extended European Search Report mailed Jul. 29, 2024, Applicant RefleXion Medical, Inc., 5 pages.

Gregoire, V. et al. (Jan. 2007). "PET-based treatment planning in radiotherapy: a new standard?" J. Nucl. Med. 48(Suppl 1): 68S-77S.

PCT Application No. PCT/US2023/079652, International Search Report and Written Opinion mailed Apr. 26, 2024, Applicant RefleXion Medical, Inc., 16 pages.

PCT Application No. PCT/US2024/021603, International Search Report and Written Opinion mailed Jul. 18, 2024, Applicant RefleXion Medical, Inc., 10 pages.

Shalchian, B. et al. (Dec. 2009). "Assessment of the Wavelet Transform in Reduction of Noise from Simulated PET Images," Journal of Nuclear Medicine Technology 37(4): 223-228.

Staff, N.R.C. (1996). "Mathematics and Physics of Emerging Bio-medical imaging," National Academies Press, Washington, D.C., 261 pages.

U.S. Appl. No. 17/571,273, Supplemental Notice of Allowability mailed Aug. 8, 2024, Inventor VORONENKO, Yevgen et al., 2 pages.

U.S. Appl. No. 17/855,691, Corrected Notice of Allowability mailed Nov. 4, 2025, Inventor Voronenko, Yevgen et al., 3 pages.

U.S. Appl. No. 17/485,059, Final Office Action mailed Jul. 1, 2024, Inventor Mazin, Samuel et al., 10 pages.

U.S. Appl. No. 17/855,691, Final Office Action mailed May 14, 2025, Inventor Voronenko, Yevgen et al., 14 pages.

U.S. Appl. No. 17/485,059, Non-Final Office Action mailed Dec. 13, 2023, Inventor Mazin, Samuel et al., 10 pages.

U.S. Appl. No. 18/178,431, Non-Final Office Action mailed Jan. 16, 2024, Inventor Mazin, Samuel, 16 pages.

U.S. Appl. No. 17/855,691, Non-Final Office Action mailed Sep. 23, 2024, Inventor Voronenko, Yevgen et al., 15 pages.

U.S. Appl. No. 18/181,147, Non-Final Office Action mailed Jun. 2, 2025, Inventor Voronenko, Yevgen et al., 7 pages.

U.S. Appl. No. 18/456,396, Non-Final Office Action mailed Aug. 12, 2025, Inventor Voronenko, Yevgen et al., 11 pages.

U.S. Appl. No. 18/624,010, Non-Final Office Action mailed Oct. 8, 2025, Inventor Voronenko, Yevgen et al. 11 pages.

U.S. Appl. No. 17/375,586, Notice of Allowance mailed Dec. 13, 2023, Inventor Janardhanan, Jayakrishnan et al., 12 pages.

U.S. Appl. No. 18/178,431, Notice of Allowance mailed Aug. 13, 2024, Inventor Mazin, Samuel, 9 pages.

U.S. Appl. No. 17/571,273, Notice of Allowance mailed May 9, 2024, Inventor Voronenko, Yevgen et al., 15 pages.

U.S. Appl. No. 18/163,176, Notice of Allowance mailed Oct. 21, 2024, Inventor Voronenko, Yevgen, 8 pages.

U.S. Appl. No. 18/163, 176, Notice of Allowance mailed Nov. 13, 2024, Inventor Voronenko, Yevgen, 7 pages.

U.S. Application No. 18/181, 147, Notice of Allowance mailed Sep. 23, 2025, Inventor Voronenko Yevgen et al., 8 pages.

(56)        References Cited

OTHER PUBLICATIONS

Yang, J. et al. (Feb. 2014). "The potential of positron emission tomography for intratreatment dynamic lung tumor tracking: A phantom study," Med. Phys. 41(2):021718, 14 pages.

\* cited by examiner

<u>200</u>

| Acquire imaging data of a target region and/or a target region surrogate | 202 |

| Acquire position and/or motion data from the target region surrogate | 204 |

| Define a target region range of motion and a corresponding target region surrogate range of motion based on the imaging data and/or target region surrogate data | 206 |

| Calculate the location of a center of motion (COM) of the target region range of motion | 208 |

| Determine a correlation between a displacement of the target region from the COM location and the target surrogate position data | 210 |

| Acquire position data from the target region surrogate | 212 |

| Determine displacement shift vector(s) of the target region from the COM location based on the correlation between the displacement of the target region from the COM location and the position data of the target region surrogate | 214 |

| Calculate a target region location by combining the location of the center of motion with the displacement shift vector(s) | 216 |

| Deliver radiation to the target region location | 218 |

| Acquire additional target region imaging data and/or position data from the target region surrogate during the treatment session | 220 |

FIG. 2A

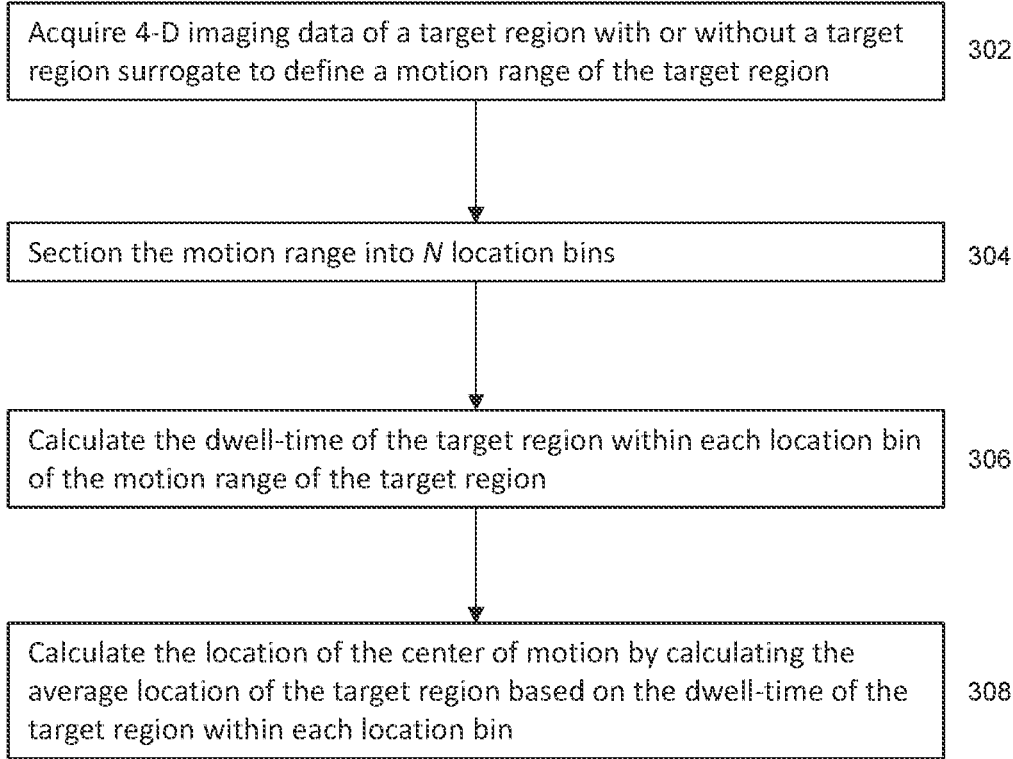

<u>300</u>

Acquire 4-D imaging data of a target region with or without a target region surrogate to define a motion range of the target region — 302

Section the motion range into $N$ location bins — 304

Calculate the dwell-time of the target region within each location bin of the motion range of the target region — 306

Calculate the location of the center of motion by calculating the average location of the target region based on the dwell-time of the target region within each location bin — 308

Acquire 4-D imaging data of a target region and of a target region surrogate to define a motion range of the target region and a motion range of the target region surrogate          402

Measure target region motion amplitude/extents of the target region motion range along IEC-X, IEC-Y, IEC-Z axes $$X_T^{ref}, Y_T^{ref}, Z_T^{ref}$$

404

Measure target region surrogate motion amplitude/extents of the target region surrogate motion range along IEC-X, IEC-Y, IEC-Z axes $$X_S^{ref}, Y_S^{ref}, Z_S^{ref}$$

406

Generate scaling factors $m_X, m_Y, m_Z$ by calculating the ratios of the target region motion amplitude to the target region surrogate motion amplitude along each axis $$m_X = \frac{X_T^{ref}}{X_S^{ref}}, m_Y = \frac{Y_T^{ref}}{Y_S^{ref}}, m_Z = \frac{Z_T^{ref}}{Z_S^{ref}}$$

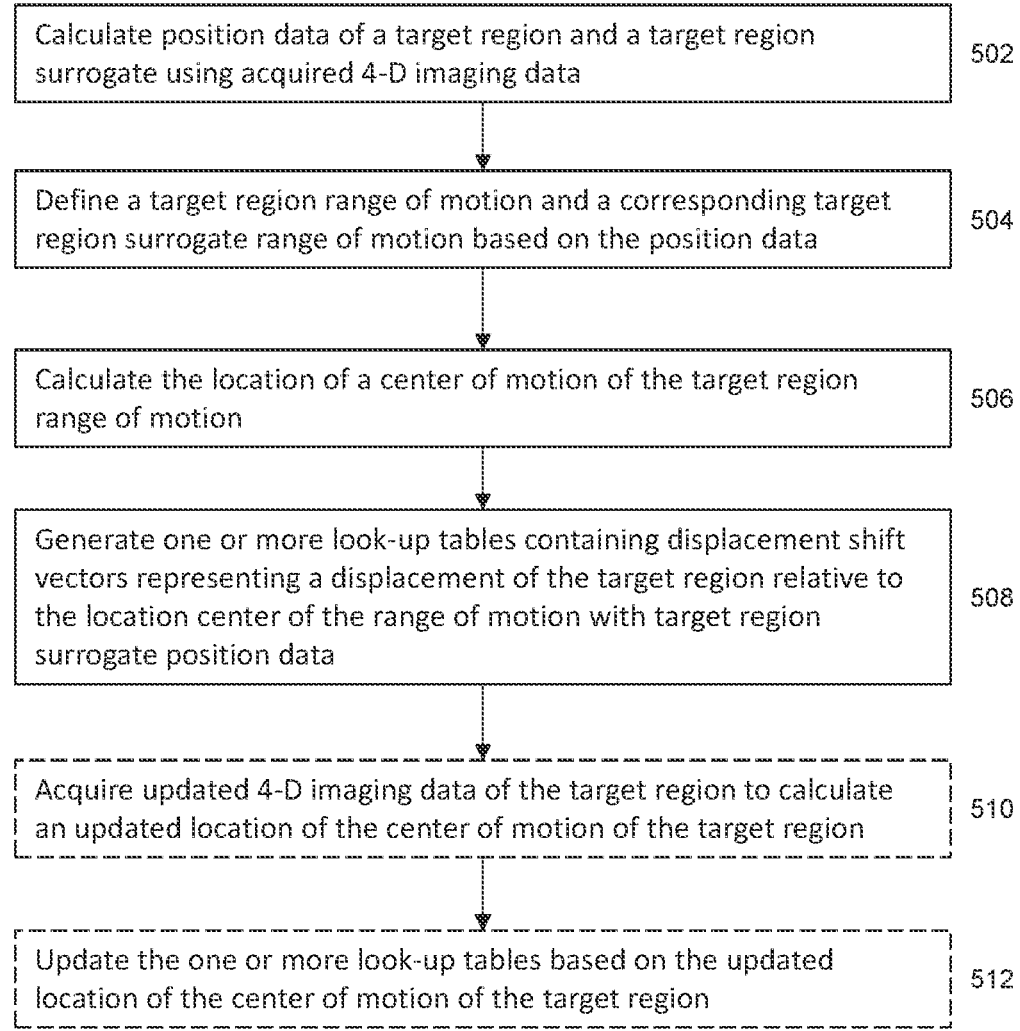

Calculate position data of a target region and a target region surrogate using acquired 4-D imaging data — 502

Define a target region range of motion and a corresponding target region surrogate range of motion based on the position data — 504

Calculate the location of a center of motion of the target region range of motion — 506

Generate one or more look-up tables containing displacement shift vectors representing a displacement of the target region relative to the location center of the range of motion with target region surrogate position data — 508

Acquire updated 4-D imaging data of the target region to calculate an updated location of the center of motion of the target region — 510

Update the one or more look-up tables based on the updated location of the center of motion of the target region — 512

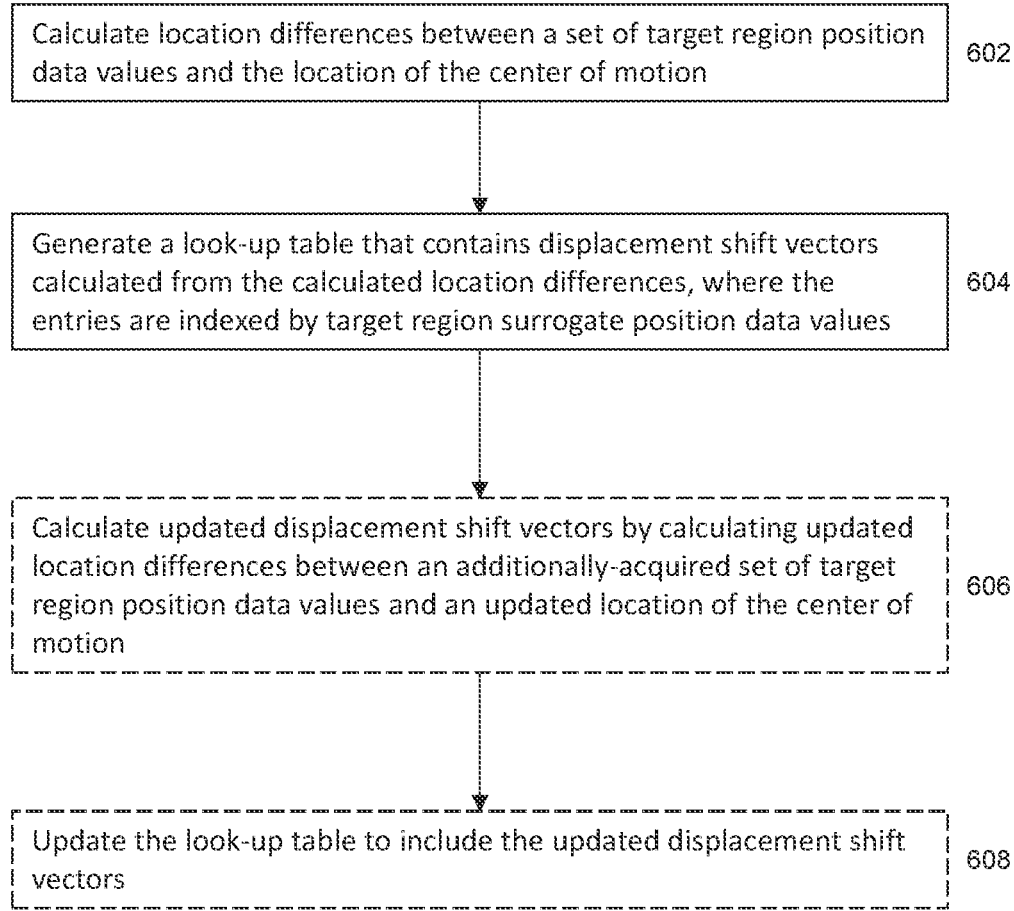

Calculate location differences between a set of target region position data values and the location of the center of motion    602

Generate a look-up table that contains displacement shift vectors calculated from the calculated location differences, where the entries are indexed by target region surrogate position data values    604

Calculate updated displacement shift vectors by calculating updated location differences between an additionally-acquired set of target region position data values and an updated location of the center of motion    606

Update the look-up table to include the updated displacement shift vectors    608

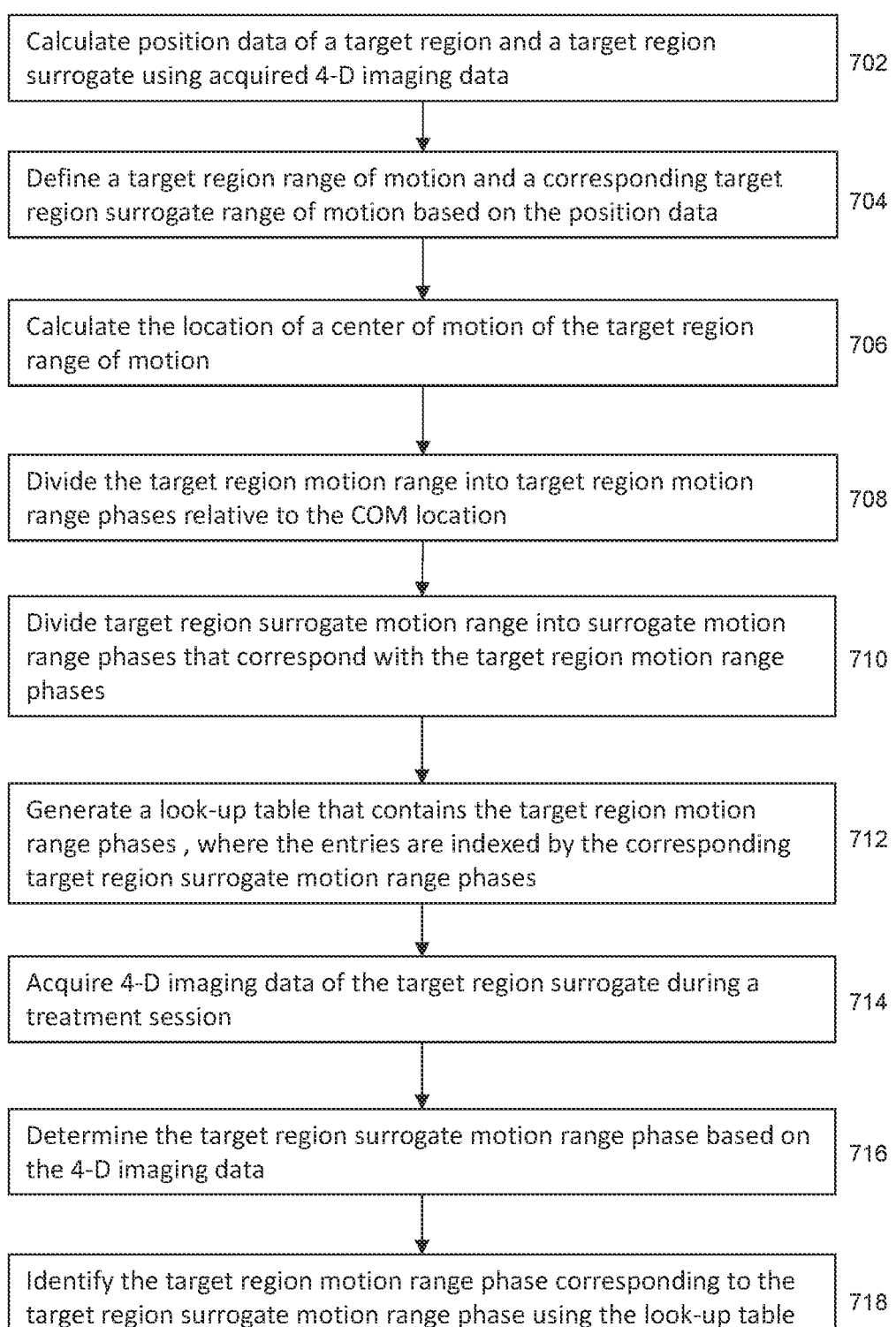

Calculate position data of a target region and a target region surrogate using acquired 4-D imaging data — 702

Define a target region range of motion and a corresponding target region surrogate range of motion based on the position data — 704

Calculate the location of a center of motion of the target region range of motion — 706

Divide the target region motion range into target region motion range phases relative to the COM location — 708

Divide target region surrogate motion range into surrogate motion range phases that correspond with the target region motion range phases — 710

Generate a look-up table that contains the target region motion range phases , where the entries are indexed by the corresponding target region surrogate motion range phases — 712

Acquire 4-D imaging data of the target region surrogate during a treatment session — 714

Determine the target region surrogate motion range phase based on the 4-D imaging data — 716

Identify the target region motion range phase corresponding to the target region surrogate motion range phase using the look-up table — 718

FIG. 7

METHODS FOR TUMOR TRACKING

CROSS-REFERENCE TO RELATED APPLICATIONS

This application is a bypass continuation of PCT Patent Application No. PCT/US2021/057948, filed Nov. 3, 2021, which is hereby incorporated herein by reference in its entirety, and which claims priority to U.S. Provisional Patent Application No. 63/109,742 filed Nov. 4, 2020, the disclosure of which is hereby incorporated by reference in its entirety.

TECHNICAL FIELD

This disclosure relates to methods for dynamically tracking a tumor based on its center of motion (COM) and/or using limited tumor imaging or position data.

BACKGROUND

The objective of radiotherapy is to deliver lethal doses of radiation to tumors while limiting the radiation exposure to healthy tissue. Ideally, the location of a tumor is always precisely known so that the therapeutic radiation source may always be focused on the tumor. However, a substantial amount of data may be needed to determine the exact location of the tumor at the time of treatment. While such data is being amassed, the tumor may be continuously moving, and the resultant data may be "smeared" or "motion-averaged", which may not provide the precise localization data needed for focused delivery of radiation. For example, traditional high-resolution images (e.g., MRI images, PET images) require relatively long periods of image data acquisition (e.g., on the order of at least 0.5 min or more, typically several minutes), which can result in blurred images of moving tumors and/or a delayed latency between image data acquisition and radiation delivery.

Other tumor tracking methods use fiducials that are implanted at the tumor site, where the fiducial provides a continuous stream of tumor position information. Examples of fiducials include radiopaque markers, electromagnetic markers, radioactive markers. Radioactive markers may continuously emit a detectable signal that indicates its position within the patient, while the location of radiopaque and/or electromagnetic markers may be detected using X-rays (e.g., using a kV CT imaging system). However, an implantable fiducial often involves an additional invasive procedure that could include an incision and/or needle puncture, which may not be appropriate for a patient depending on the location of the tumor. Less invasive tumor tracking methods may use breathing monitors that include cameras and/or spirometers that monitor the location of an externally-placed device (e.g., temporarily attached to a patient's skin or placed on their body), and use the position of the external device directly as a surrogate for the position of an internal tumor. However, the correlation between the external surrogate position and the internal tumor position may change during a treatment session, e.g. when the patient relaxes during treatment and shifts the tumor motion range. Accordingly, improved methods of quickly and precisely tracking the location of a tumor at the time of radiotherapy are desired.

SUMMARY

Disclosed herein are methods for determining the location of a moving target region (e.g., a tumor) based on the location of the center of its range of motion and the location of a target region surrogate, during a radiotherapy treatment session and/or a non-therapeutic procedure such as a quality assurance (QA) session. A QA session is one in which a treatment plan and/or radiotherapy system is evaluated to determine whether the treatment plan delivers the prescribed dose and/or whether the radiotherapy system is able to function precisely to deliver radiation according to the treatment plan. A QA session does not involve a patient. In some variations, a QA session may include a phantom in the treatment area while in other variations, a QA session may be phantom-less. The methods described herein may comprise characterizing the motion range of the target region relative to a "center of motion" (COM), and determining a correlation between the position of the target region surrogate and the displacement of the target region from the center of the motion range as the target region moves. Calculating the location of the center of motion (COM) of the target region and determining the correlation between the target region position (relative to the location of the COM) and the target region surrogate position may be performed before a treatment session (e.g., during treatment planning) and/or at the start of a treatment session, and/or at various timepoints during a treatment session. Once the location of the COM has been determined, the position of the target region can be calculated based on the COM location and position data from the target region surrogate. Optionally, methods may comprise determining a correlation between the phase of the target region surrogate and the position (e.g., displacement) of the target region relative to the location of the COM. In some variations, the target region surrogate may be frequently or continuously providing position data to the radiotherapy system, and using the methods described herein, the location of the target region may be frequently or continuously updated during a treatment session. The methods disclosed herein may facilitate the real-time tracking of a target region when there is insufficient position and/or imaging data to directly identify the real-time location of the target region centroid (e.g., target region center-of-mass).

One variation of a method for determining a target region location (which may be used in therapeutic or non-therapeutic applications) may comprise using acquired imaging data to calculate a center of motion location of a target region, acquiring position data from a target region surrogate, determining a displacement shift vector of the target region from the center of motion location based on the target region surrogate position data, and calculating a target region location by combining the center of motion location with the displacement shift vector. The target region may be a tumor. The target region surrogate may comprise a breathing surrogate. For example, the target region surrogate may comprise one or more of an infrared reflector block, an implantable RF-emitting fiducial marker, and a radiation-emitting source. In one variation, the radiation-emitting source may be an X-ray emitting source and acquiring position data may comprise acquiring X-ray detector data. Alternatively, or additionally, the radiation-emitting source may be a photon-emitting source and acquiring position data may comprise acquiring single-photon emission detector data. In some variations, the radiation-emitting source may be a positron-emitting source and acquiring position data may comprise acquiring PET detector data. Acquiring position data may comprise acquiring optical camera images of a patient's skin surface. The acquired imaging data may comprise one or more of X-ray, SPECT, MRI, and/or PET imaging data. Calculating the center of motion location may comprise acquiring imaging data over an interval of time to define a range of motion of the target region. The interval of time may include multiple periods of a breathing cycle. The acquired imaging data may comprise imaging data of the target region, and/or imaging data of the target region surrogate. In a non-therapeutic application (e.g., a QA session), a phantom comprising a region that mimics the target region may be placed in the treatment area instead of a patient. The phantom may be located on a motion stage with a controller that moves the phantom according to motion trajectories that mimic patient motion, such breathing and/or digestive motion, and/or whole body shifts. Some variations may comprise tracking a region in the phantom (e.g., the mimicked target region) using the methods described herein and comparing the calculated location data with the true location data provided by the motion stage controller.

In some variations, calculating the center of motion location ($\overline{X}$, $\overline{Y}$, $\overline{Z}$) may further comprise sectioning the motion range into a number N of location bins ($X_i$, $Y_i$, $Z_i$), calculating a dwell-time ($t_i$) of the target region within each location bin, and calculating the center of motion location by calculating the average location of the target region using the dwell-time of the target region within each location bin ($X_i$, $Y_i$, $Z_i$):

$$\overline{X} = \frac{\sum_{i=1}^{N} X_i \cdot t_i}{\sum_{i=1}^{N} t_i}; \quad \overline{Y} = \frac{\sum_{i=1}^{N} Y_i \cdot t_i}{\sum_{i=1}^{N} t_i}; \quad \overline{Z} = \frac{\sum_{i=1}^{N} Z_i \cdot t_i}{\sum_{i=1}^{N} t_i}$$

The interval of time may be about 10 minutes or less, about 3 minutes or less, about 1 minute or less. Defining the motion range of the target region may use 4-D imaging data, for example, 4-D PET/CT imaging data.

Some methods may further comprise calculating a coefficient based on a target region motion amplitude and a target region surrogate motion amplitude, and determining the displacement shift vector may comprise scaling the position data by the coefficient. For example, calculating the coefficient may comprise acquiring imaging data of the target region and of the target region surrogate over an interval of time, measuring the target region motion amplitude and the target region surrogate motion amplitude using the acquired imaging data, and calculating the coefficient by taking a ratio of the target region motion amplitude and the target region surrogate motion amplitude. Measuring the target region motion amplitude may comprise measuring target region motion extents along X, Y, Z axes ($X_T^{ref}$, $Y_T^{ref}$, $Z_T^{ref}$), measuring the target region surrogate motion amplitude comprises measuring the target region surrogate motion extents along X, Y, Z axes ($X_S^{ref}$, $Y_S^{ref}$, $Z_S^{ref}$). Calculating the coefficient may comprise calculating a coefficient ($m_X$, $m_Y$, $m_Z$) for each of the X, Y, Z axes:

$$m_X = \frac{X_T^{ref}}{X_S^{ref}}, \quad m_Y = \frac{Y_T^{ref}}{Y_S^{ref}}, \quad m_Z = \frac{Z_T^{ref}}{Z_S^{ref}}$$

Determining the displacement shift vector may comprise scaling the position data by the calculated coefficients ($m_X$, $m_Y$, $m_Z$) for each of the X, Y, Z axes. In some variations, combining the center of the motion location with the displacement shift vector comprises shifting the center of motion location by the scaled position data to calculate the updated target region location.

Alternatively, or additionally, in some variations, determining the displacement shift vector comprises using the acquired position data to select a shift factor from a look-up table (LUT) that contains shift factors and is indexed by target region surrogate locations. Combining the center of the motion location with the displacement shift vector may comprise shifting the center of motion location by the selected shift factor to calculate the updated target region location. Optionally, some variations may comprise delivering radiation to the target region location and/or may comprise acquiring updated target region imaging data and updating the center of motion location of the target region based on the acquired updated target region imaging data. Some variations may further comprise acquiring additional target region surrogate position data, and updating the displacement shift vector based on the acquired additional target region surrogate position data. In some variations, calculating the target region location may comprise determining a breathing phase based on the acquired position data, and mapping the breathing phase with a corresponding displacement vector of the target region. The mapping between the breathing phase and the displacement vector of the target region location may be determined by the acquired imaging data of the target region and previously-acquired breathing surrogate position data.

Another variation of a method for determining a target region location (which may be used in therapeutic or non-therapeutic applications) may comprise defining a range of motion of a target region based on acquired imaging data, where the range of motion comprises a plurality of phases corresponding to locations of the target region relative to a center of motion of the target region, acquiring position data from a target region surrogate, and determining a target region location by mapping the surrogate position data to one of the plurality of motion range phases to identify the corresponding target region location. The target region surrogate may comprise a breathing surrogate, the target region motion may correspond with breathing motion, and the plurality of phases may correspond with breathing phases. The mapping between each of the breathing phases and the corresponding target region location may be determined by the acquired imaging data of the target region motion and previously-acquired breathing surrogate motion data. The acquired imaging data and the previously-acquired breathing surrogate data may comprise 4-D imaging data, and may comprise, for example, 4-D PET/CT imaging data. The center of motion of the target region may be a location within the target region motion range calculated from an average of target region positions over dwell times of the target region at those target region positions.

Also disclosed herein is a method for generating a motion model, which may be used in therapeutic or non-therapeutic applications. One variation of a method for generating a motion model may comprise calculating a center of motion location ($\overline{X}$, $\overline{Y}$, $\overline{Z}$) of a target region based on acquired imaging data, acquiring motion data ($X_s(t)$, $Y_s(t)$, $Z_s(t)$) from a target region surrogate, determining a target region motion amplitude ($X_T^{Ref}$) from the acquired imaging data and a target region surrogate motion amplitude ($X_S^{Ref}$) from the motion data, and generating a target region motion model ($X_T(t)$, $Y_T(t)$, $Z_T(t)$) that includes a coefficient ($m_X$, $m_Y$, $m_Z$) calculated based on the target region motion amplitude and the target region surrogate motion amplitude, where:

$$X_T(t) = \overline{X} + m_X X_s(t)$$

$$Y_T(t)=\overline{Y}+m_y Y_s(t)$$

$$Z_T(t)=\overline{Z}+m_z Z_s(t)$$

The surrogate motion data may comprise surrogate position data. In some variations, the target region surrogate may comprise a breathing surrogate. The target region surrogate may comprise one or more of an infrared reflector block, an implantable RF-emitting fiducial marker, and a radiation-emitting source. In one variation, the radiation-emitting source may be an X-ray emitting source and acquiring position data may comprise acquiring X-ray detector data. Alternatively, or additionally, the radiation-emitting source may be a photon-emitting source and acquiring position data may comprise acquiring single-photon emission detector data. In some variations, the radiation-emitting source may be a positron-emitting source and acquiring position data may comprise acquiring PET detector data. Acquiring position data may comprise acquiring optical camera images of a patient's skin surface. The acquired imaging data may comprise one or more of X-ray, SPECT, MRI, and/or PET imaging data. Calculating the center of motion location may comprise acquiring imaging data over an interval of time. For example, the interval of time may include multiple periods or cycles of a breathing cycle. The acquired imaging data may comprise imaging data of the target region, and/or imaging data of the target region surrogate.

In some variations, calculating the center of motion location ($\overline{X}$, $\overline{Y}$, $\overline{Z}$) may further comprise sectioning the motion range into a number N of location bins ($X_i$, $Y_i$, $Z_i$), calculating a dwell-time ($t_i$) of the target region within each location bin, and calculating the center of motion location by calculating the average location of the target region using the dwell-time of the target region within each location bin ($X_i$, $Y_i$, $Z_i$):

$$\overline{X} = \frac{\sum_{i=1}^{N} X_i \cdot t_i}{\sum_{i=1}^{N} t_i}; \overline{Y} = \frac{\sum_{i=1}^{N} Y_i \cdot t_i}{\sum_{i=1}^{N} t_i}; \overline{Z} = \frac{\sum_{i=1}^{N} Z_i \cdot t_i}{\sum_{i=1}^{N} t_i}$$

The interval of time may be about 10 minutes or less, about 3 minutes or less, about 1 minute or less. Defining the motion range of the target region may use 4-D imaging data, for example, 4-D PET/CT imaging data. The plurality of location bins may correspond with breathing phases, and the method may further comprise generating a mapping between each of the breathing phases and a corresponding displacement vector of the target region. Generating the mapping between each breathing phase and the corresponding displacement vector of the target region location may be based on the acquired imaging data and the acquired motion data of the breathing surrogate. The acquired imaging data and the acquired motion data may comprise 4-D imaging data, for example, 4-D PET/CT imaging data.

In some variations, determining the target region motion amplitude ($X_T^{Ref}$) and the target region surrogate motion amplitude ($X_S^{Ref}$) may comprise acquiring imaging data of the target region and of the target region surrogate over an interval of time, measuring the target region motion amplitude and the target region surrogate motion amplitude using the acquired imaging data, and calculating the coefficient by taking a ratio of the target region motion amplitude and the target region surrogate motion amplitude. Measuring the target region motion amplitude may comprise measuring target region motion extents along X, Y, Z axes ($X_T^{ref}$, $Y_T^{ref}$, $Z_T^{ref}$), and measuring the target region surrogate motion amplitude may comprise measuring the target region surrogate motion extents along X, Y, Z axes ($X_S^{ref}$, $Y_S^{ref}$, $Z_S^{ref}$). Calculating the coefficient may comprise calculating a coefficient ($m_X$, $m_Y$, $m_Z$) for each of the X, Y, Z axes:

$$m_X = \frac{X_T^{ref}}{X_S^{ref}}, m_Y = \frac{Y_T^{ref}}{Y_S^{ref}}, m_Z = \frac{Z_T^{ref}}{Z_S^{ref}}$$

Also disclosed herein is a method for mapping a position of a target region with a position of a target region surrogate, which may be used in therapeutic or non-therapeutic applications. In one variation, the method may comprise calculating a center of motion location ($\overline{X}$, $\overline{Y}$, $\overline{Z}$) of a target region based on acquired imaging data, acquiring motion data ($X_s(t)$, $Y_s(t)$, $Z_s(t)$) from a target region surrogate, and generating one or more look-up tables ($LUT_x$, $LUT_y$, $LUT_z$) containing displacement shift vectors indexed by target region surrogate locations. The displacement shift vectors may designate target region locations relative to the center of the motion range of the target region. The surrogate motion data may comprise surrogate position data. In some variations, the target region surrogate may comprise a breathing surrogate. For example, the target region surrogate may comprise one or more of an infrared reflector block, an implantable RF-emitting fiducial marker, and a radiation-emitting source. In one variation, the radiation-emitting source may be an X-ray emitting source and acquiring position data may comprise acquiring X-ray detector data. Alternatively, or additionally, the radiation-emitting source may be a photon-emitting source and acquiring position data may comprise acquiring single-photon emission detector data. In some variations, the radiation-emitting source may be a positron-emitting source and acquiring position data may comprise acquiring PET detector data. Acquiring position data may comprise acquiring optical camera images of a patient's skin surface. The acquired imaging data may comprise one or more of X-ray, SPECT, MRI, and/or PET imaging data. Calculating the center of motion location may comprise acquiring imaging data over an interval of time. The interval of time may include multiple periods of a breathing cycle. The acquired imaging data may comprise imaging data of the target region, and/or imaging data of the target region surrogate.

In some variations, calculating the center of motion location ($\overline{X}$, $\overline{Y}$, $\overline{Z}$) may further comprise sectioning the motion range into a number N of location bins ($X_i$, $Y_i$, $Z_i$), calculating a dwell-time ($t_i$) of the target region within each location bin, and calculating the center of motion location by calculating the average location of the target region using the dwell-time of the target region within each location bin ($X_i$, $Y_i$, $Z_i$):

$$\overline{X} = \frac{\sum_{i=1}^{N} X_i \cdot t_i}{\sum_{i=1}^{N} t_i}; \overline{Y} = \frac{\sum_{i=1}^{N} Y_i \cdot t_i}{\sum_{i=1}^{N} t_i}; \overline{Z} = \frac{\sum_{i=1}^{N} Z_i \cdot t_i}{\sum_{i=1}^{N} t_i}$$

The interval of time may be about 10 minutes or less, about 3 minutes or less, about 1 minute or less. Defining the motion range of the target region may use 4-D imaging data, for example, 4-D PET/CT imaging data. The plurality of location bins may correspond with breathing phases, and the method may further comprise generating a mapping between each of the breathing phases and a corresponding displacement shift vector of the target region. Generating the mapping between each breathing phase and its corresponding displacement shift vector of the target region is based on the acquired imaging data and the acquired motion data of the breathing surrogate. The acquired imaging data and the acquired motion data may comprise 4-D imaging data, such as 4-D PET/CT imaging data.

In some variations, the displacement shift vectors may comprise scaling coefficients, and the method may further comprise generating a target region motion model $(X_T(t), Y_T(t), Z_T(t))$. The motion model may comprise:

$$X_T(t)=\bar{X}+LUT_x(X_s(t))^*X_s(t)$$

$$Y_T(t)=\bar{Y}+LUT_y(Y_s(t))^*Y_s(t)$$

$$Z_T(t)=\bar{Z}+LUT_z(Z_s(t))^*Z_s(t)$$

The displacement shift vectors may comprise shift factors, and the method may further comprise generating a target region motion model $(X_T(t), Y_T(t), Z_T(t))$. The motion model may comprise:

$$X_T(t)=\bar{X}+LUT_x(X_s(t))$$

$$Y_T(t)=\bar{Y}+LUT_y(Y_s(t))$$

$$Z_T(t)=\bar{Z}+LUT_z(Z_s(t))$$

Also disclosed herein is a radiotherapy system comprising one or more processors and one or more machine-readable memories in communication with the one or more processors, the one or more machine-readable memories storing instructions which, when executed, cause the processor to perform a method according to any of the methods disclosed above or hereinafter.

BRIEF DESCRIPTION OF THE DRAWINGS

FIG. 2A depicts a flowchart representation of one variation of a method for determining a target region position.

FIG. 3 depicts a flowchart representation of one variation of a method for calculating the center of motion (COM) location of a target region.

FIG. 4 depicts a flowchart representation of one variation of a method for calculating a scaling factor or coefficient.

FIG. 5 depicts a flowchart representation of one variation of a method for generating a database of displacement shift vectors.

FIG. 6 depicts a flowchart representation of one variation of a method for calculating the displacement shift vectors.

FIG. 7 depicts a flowchart representation of one variation of a method for determining the location of a target region based on a surrogate's motion phase.

DETAILED DESCRIPTION

Figure 1A:
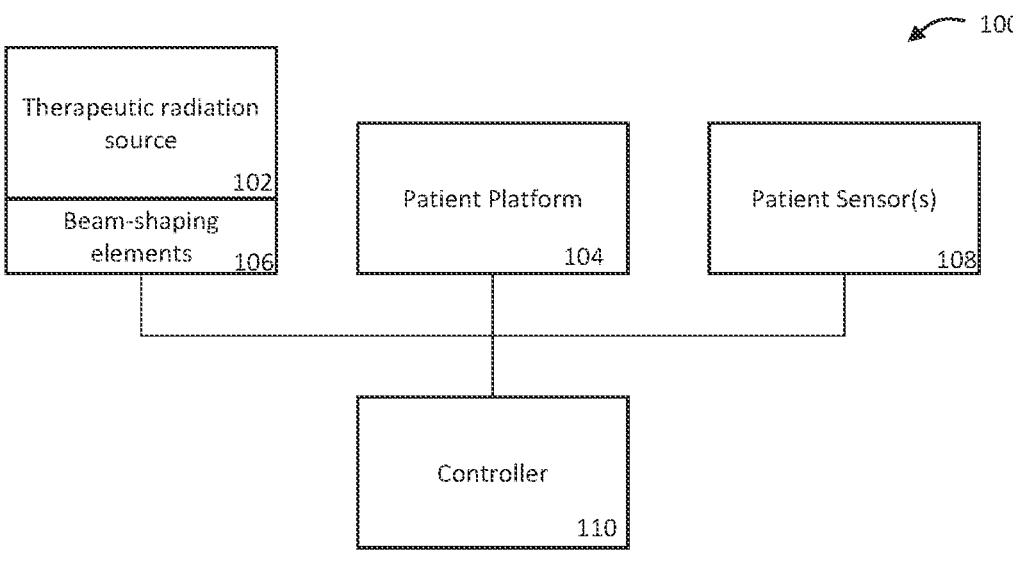
FIG. 1A depicts a functional block diagram of a radiotherapy system.

Described herein are methods for determining the location of one or more target regions during a radiotherapy treatment session or a radiotherapy quality assurance (QA) session. These methods may facilitate the precise tracking of a target region when there is insufficient imaging or position data to directly identify the centroid (e.g., center of mass) of the target region. In some variations, methods may comprise calculating center of the motion range (COM) of the target region, and determining a correlation between the position of the target region surrogate and the displacement of the target region from the center of the motion range as the target region moves. The center of motion of a target region refers to the central point of the target region's motion range. In some variations, a target region's motion may be cyclical (e.g., repetitive, periodic), due to physiological processes that may also be cyclical (e.g., breathing, heart beating, etc.). The center of motion of a target region is different from the center of mass of a target region. The center of mass refers to the location of the physical extent of the target region (rather than its motion). As an analogy for the sake of explanation, if the target region were the moon, the location of its center of motion would be the location of the center of the moon's trajectory around the earth (i.e., somewhere in the middle of the earth), while the location of the center of mass would be the location of the moon itself (which would vary as the moon revolves around the earth). During a treatment session, the location of the COM may be determined during patient setup and target localization, and the target region surrogate (e.g., a breathing monitor) may continuously provide position data to the radiotherapy system controller. The radiotherapy system controller may then use the predetermined correlation between the position of the target region surrogate and the displacement of the target region from the location of the COM to calculate the location of the target region. Optionally, the location of the COM may be updated during the treatment session. This method may help facilitate precise localization of the target region when there may be sparse (if any) direct imaging data of the target region (i.e., where the target region is in the field-of-view of the image), but position data from a target region surrogate may be readily and/or continuously available. The readily and/or continuously available position data from the target region surrogate may also help promote more frequent, and/or even continuous, updates and/or tracking of a target region's location.

This method may also help facilitate determining the location of the target region using time-averaged or motion-blurred images (which may be used to calculate the center of motion), without the need to calculate the location of the center of mass of the target region. In most cases, there is insufficient data in time-averaged or motion-blurred images to precisely determine the location of a tumor's center of mass or centroid. Typically, identifying the location of the center of mass of a moving target region requires the acquisition of larger quantities of imaging data, often at high acquisition rates and/or high resolution. However, such imaging data is not usually readily available during a treatment session, especially for stochastic imaging modalities (such as PET imaging), and as such, the location of a tumor centroid is difficult to precisely determine from in-treatment imaging data. The methods described herein leverage tumor and surrogate position and/or motion data that is known before a treatment session, and then updates judiciously during a treatment session to obtain current tumor position. That is, previously-acquired imaging data may be used to calculate a correlation between a tumor's displacement from the center of motion (and not the tumor's centroid) and a surrogate's position and/or motion. Since the location of the center of motion can be determined from time-averaged and/or motion-blurred and/or sparse images, as well as surrogate data, are readily available during a treatment session, the methods described herein may be able to precisely locate a tumor without having to calculate the tumor's centroid.

Radiotherapy Systems

The methods for dynamically tracking the location of a target region during a treatment session described herein may be used with any external beam radiotherapy system that comprises a movable therapeutic radiation source, an imaging system, and an optional target region surrogate. FIG. 1A is a block diagram representation of an external beam radiotherapy system. Radiotherapy system (100) comprises one or more therapeutic radiation sources (102) and a patient platform (104). The therapeutic radiation source can be used in a therapeutic context, for example during a treatment session, and in non-therapeutic contexts, such as during a QA session as previously described. The therapeutic radiation source may comprise an X-ray source, electron source, proton source, and/or a neutron source. For example, a therapeutic radiation source (102) may comprise a linear accelerator (linac), Cobalt-60 source, and/or an X-ray machine. The therapeutic radiation source may be movable about the patient platform so that radiation beams may be directed to a patient on the patient platform from multiple firing positions and/or angles. In some variations, a radiotherapy system may comprise one or more beam-shaping elements and/or assemblies (106) that may be located in the beam path of the therapeutic radiation source. For example, a radiotherapy system may comprise a linac (102) and a beam-shaping assembly (106) disposed in a path of the radiation beam. The beam-shaping assembly may comprise one or more movable jaws and a collimator, such as a multi-leaf collimator (e.g., a binary multi-leaf collimator, a 2-D multi-leaf collimator, etc.). The linac and the beam-shaping assembly may be mounted on a gantry that comprises a motion system configured to adjust the position of the linac and the beam-shaping assembly, and/or may be mounted on a support structure comprising one or more robotic arms, C-arms, gimbals, and the like. The patient platform (104) may also be movable. For example, the patient platform (104) may be configured to translate a patient linearly along a single axis of motion (e.g., along the IEC-Y axis), and/or may be configured to move the patient along multiple axes of motion (e.g., 2 or more degrees of freedom, 3 or more degrees of freedom, 4 or more degrees of freedom, 5 or more degrees of freedom, etc.). In some variations, a radiotherapy system may have a 5-DOF patient platform that is configured to move along the IEC-Y axis, the IEC-X axis, the IEC-Z axis, as well as pitch and yaw.

In the variation shown in FIG. 1, the radiotherapy system (100) also comprises a controller (110) that is in communication with the therapeutic radiation source (102), beam-shaping elements or assemblies (106), a patient platform (104), and one or more patient sensors (108) (e.g., one or more patient sensor systems). The controller (110) may comprise one or more processors and one or more machine-readable memories in communication with the one or more processors, which may be configured to execute or perform any of the methods described herein. The one or more machine-readable memories may store instructions to cause the processor to execute modules, processes and/or functions associated with the system, such as one or more treatment plans, target region surrogate data (e.g., imaging data, location/position data, motion data), the calculation of radiation fluence maps based on treatment plan and/or clinical goals, segmentation of fluence maps into radiotherapy system instructions (e.g., that may direct the operation of the gantry, therapeutic radiation source, beam-shaping assembly, patient platform, and/or any other components of a radiotherapy system), and image and/or data processing associated with treatment planning and/or radiation delivery. In some variations, the memory may store treatment plan data (e.g., treatment plan firing filters, fluence map, planning images, treatment session PET pre-scan images and/or initial CT, MRI, and/or X-ray images), target region surrogate data, instructions for processing the target region surrogate data to generate a radiation delivery fluence map, and instructions for delivering the derived fluence map (e.g., instructions for operating the therapeutic radiation source, beam-shaping assembly and patient platform in concert). The controller of a radiotherapy system may be connected to other systems by wired or wireless communication channels. For example, the radiotherapy system controller may be in wired or wireless communication with a radiotherapy treatment planning system controller such that fluence maps, firing filters, target region surrogate data, initial and/or planning images (e.g., CT images, MRI images, PET images, 4-D CT images), patient data, and other clinically-relevant information may be transferred from the radiotherapy treatment planning system to the radiotherapy system. The delivered radiation fluence, any dose calculations, and any clinically-relevant information and/or data acquired during the treatment session may be transferred from the radiotherapy system to the radiotherapy treatment planning system. This information may be used by the radiotherapy treatment planning system for adapting the treatment plan and/or adjusting delivery of radiation for a successive treatment session.

Figure 1B:
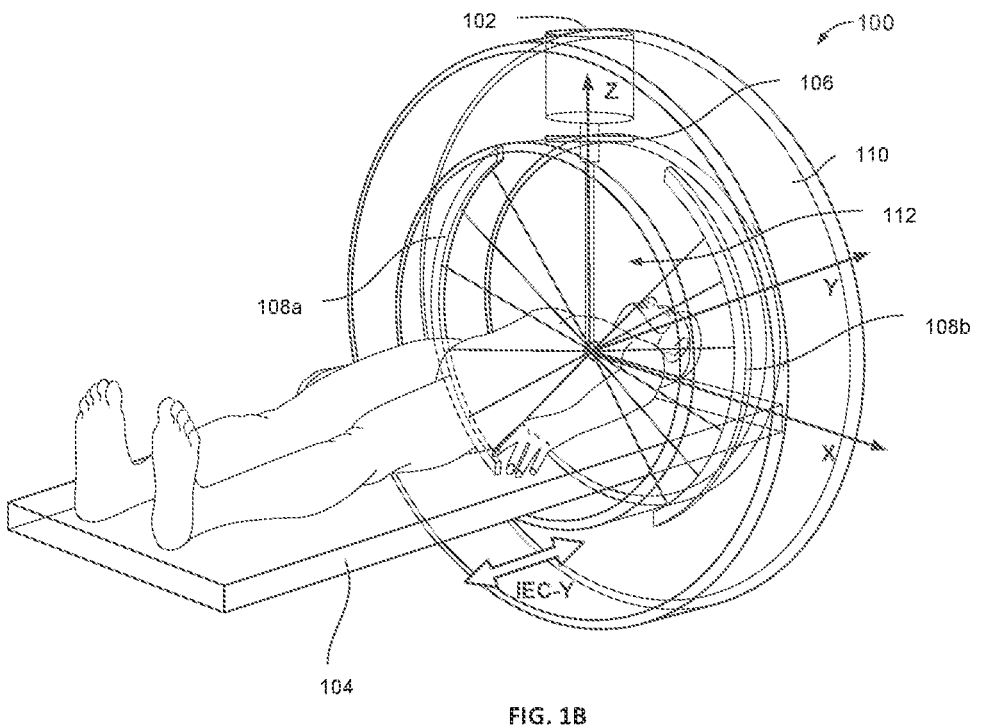
FIG. 1B depicts one variation of a radiotherapy system.

FIG. 1B depicts one variation of a radiotherapy system (100). Radiotherapy system (100) may comprise a gantry (110) rotatable about a patient treatment region (112), one or more PET detectors (108) mounted on the gantry, a therapeutic radiation source (102) mounted on the gantry, a beam-shaping module (106) disposed in the beam path of the therapeutic radiation source, and a patient platform (119) movable within the patient treatment region (112). In some variations, the gantry (110) may be a continuously-rotating gantry (e.g., able to rotate through 360° and/or in arcs with an angular spread of less than about 360°). The gantry (110) may be configured to rotate from about 20 RPM to about 70 RPM about the patient treatment region (112). For example, the gantry (110) may be configured to rotate at about 60 RPM. The gantry may also be configured to rotate at a slower rate, e.g., 20 RPM or less, 10 RPM or less, 1 RPM or less. The beam-shaping module (106) may comprise a movable jaw and a dynamic multi-leaf collimator (MLC). The beam-shaping module may be arranged to provide variable collimation width in the longitudinal direction of 1 cm, 2 cm or 3 cm at the system iso-center (e.g., a center of a patient treatment region). The jaw may be located between the therapeutic radiation source and the MLC, or may be located below the MLC. Alternatively, the beam-shaping module may comprise a split jaw where a first portion of the jaw is located between the therapeutic radiation source and the MLC, and a second portion of the jaw is located below the MLC and coupled to the first portion of the jaw such that both portions move together. The therapeutic radiation source (102) may be configured to emit radiation at predetermined firing positions (e.g., firing angles 0°/360° to 359°) about the patient treatment region (112). For example, in a system with a continuously-rotatable gantry, there may be from about 50 to about 100 firing positions (e.g., 50 firing positions, 60 firing positions, 80 firing positions, 90 firing positions, 100 firing positions, etc.) at various angular positions (e.g., firing angles) along a circle circumscribed by the therapeutic radiation source as it rotates. The firing positions may be evenly distributed such that the angular displacement between each firing position is the same.

Figure 1C:
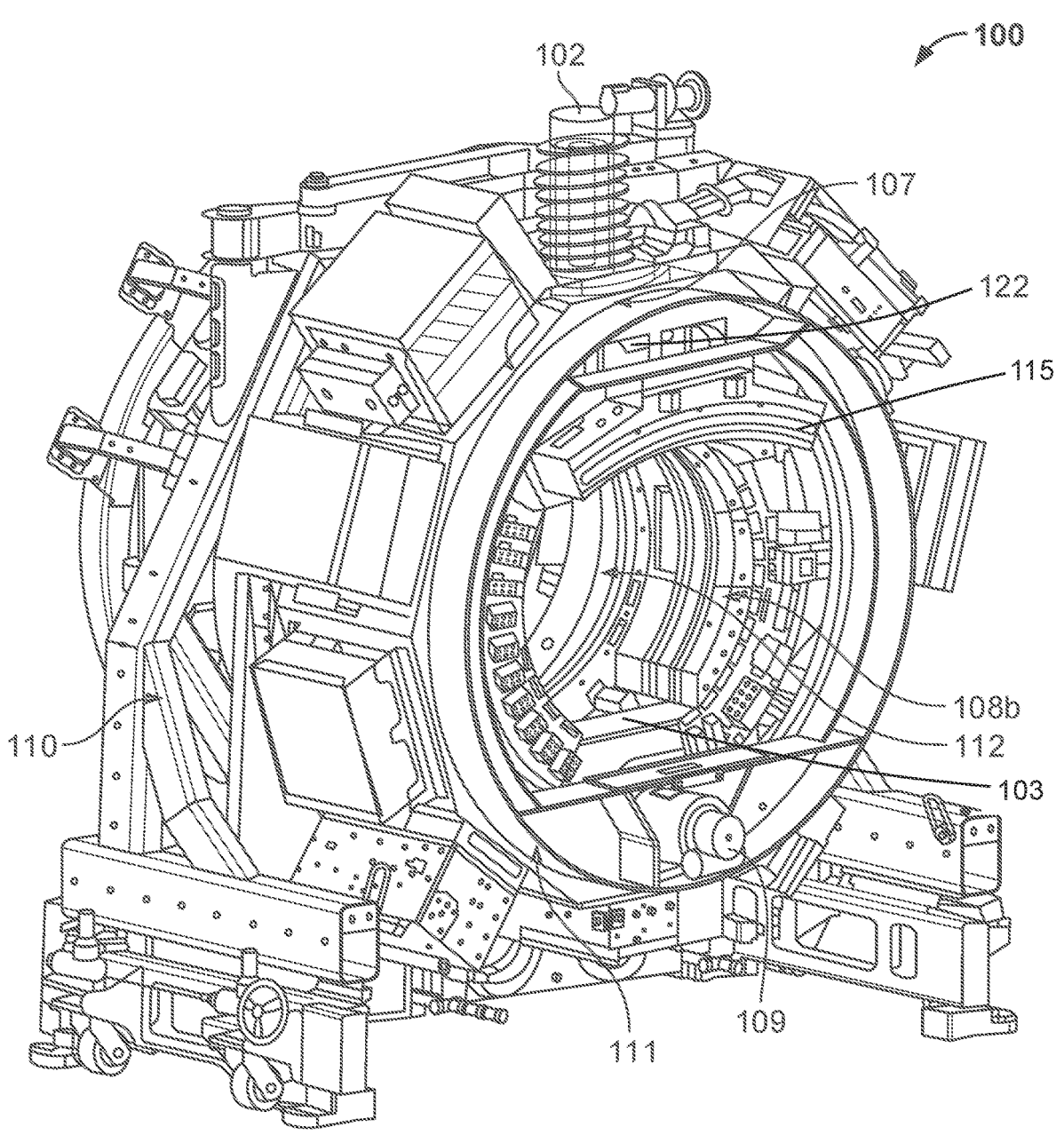
FIG. 1C depicts a perspective component view of a radiotherapy system.

FIG. 1C is a perspective component view of the radiotherapy system (100). As shown there, the beam-shaping module may further comprise a primary collimator or jaw (107) disposed above the binary MLC (122). The radiotherapy system may also comprise an MV X-ray detector (103) located opposite the therapeutic radiation source (102). Optionally, the radiotherapy system (100) may further comprise a kV CT imaging system on a rotatable ring (111) that is attached to the rotatable gantry (110) such that rotating the gantry (110) also rotates the ring (111). The kV CT imaging system may comprise a kV X-ray source (109) and an X-ray detector (115) located across from the X-ray source (109). The therapeutic radiation source or linac (102) and the PET detectors (108) may be mounted on the same cross-sectional plane of the gantry (i.e., PET detectors are co-planar with a treatment plane defined by the linac and the beam-shaping module), while the kV CT scanner and ring may be mounted on a different cross-sectional plane (i.e., not co-planar with the treatment plane). The radiotherapy system (100) of FIGS. 1B and 1C may have a first patient sensor system that comprises the kV CT imaging system and a second patient sensor system that comprises the PET detectors. Optionally, a third patient sensor system may comprise the MV X-ray source and MV detector. The patient sensor data acquired by one or more of these patient sensor systems may include X-ray and/or PET imaging data, and the radiotherapy system controller may be configured to store the acquired patient sensor data and calculate a radiation delivery fluence using the patient sensor data. In some variations, additional patient sensors, such as position sensors, may be included, and the controller may be configured to receive location and/or motion data from the position sensor and incorporate this data with other patient sensor data to calculate a radiation delivery fluence. Additional descriptions of radiotherapy systems that may be used with any of the methods described herein are provided in U.S. Pat. No. 10,695,586, filed Nov. 15, 2017.

The patient platform (104) may be movable in the treatment region (112) to discrete, pre-determined locations along IEC-Y. These discrete, pre-determined locations may be referred to as "beam stations". For example, a radiotherapy treatment planning system may specify 200 beam stations, where each beam station is about 2 mm (e.g., 2.1 mm) apart from its adjacent beam stations. During a treatment session, the radiotherapy treatment system may move the patient platform to each of the beam stations, and may stop the platform at a beam station while radiation is delivered to the patient. In some variations, after the platform has been stepped to each of the 200 beam stations in a first direction (e.g., into the bore), the platform may be stepped to each of the 200 beam stations in a second direction opposite the first direction (e.g., out of the bore, in reverse), where radiation is delivered to the patient while the platform is stopped at a beam station. Alternatively, or additionally, after the platform has been stepped to each of the 200 beam stations in a first direction (e.g., into the bore) where radiation is delivered at each of the beam stations, the platform may be moved in reverse so that it returns to the first beam station. No radiation may be delivered while the platform is moved back to the first beam station. The platform may then be stepped, for a second time, to each of the 200 beam stations in the first direction for a second pass of radiation delivery. In some variations, the platform may be moved continuously while radiation is delivered to the patient and may not be stopped at beam stations during the delivery of therapeutic radiation. Additional descriptions of patient platforms that may be used with any of the radiotherapy systems and methods described herein are provided in U.S. Pat. No. 10,702,715, filed Nov. 15, 2017.

Figure 1D:
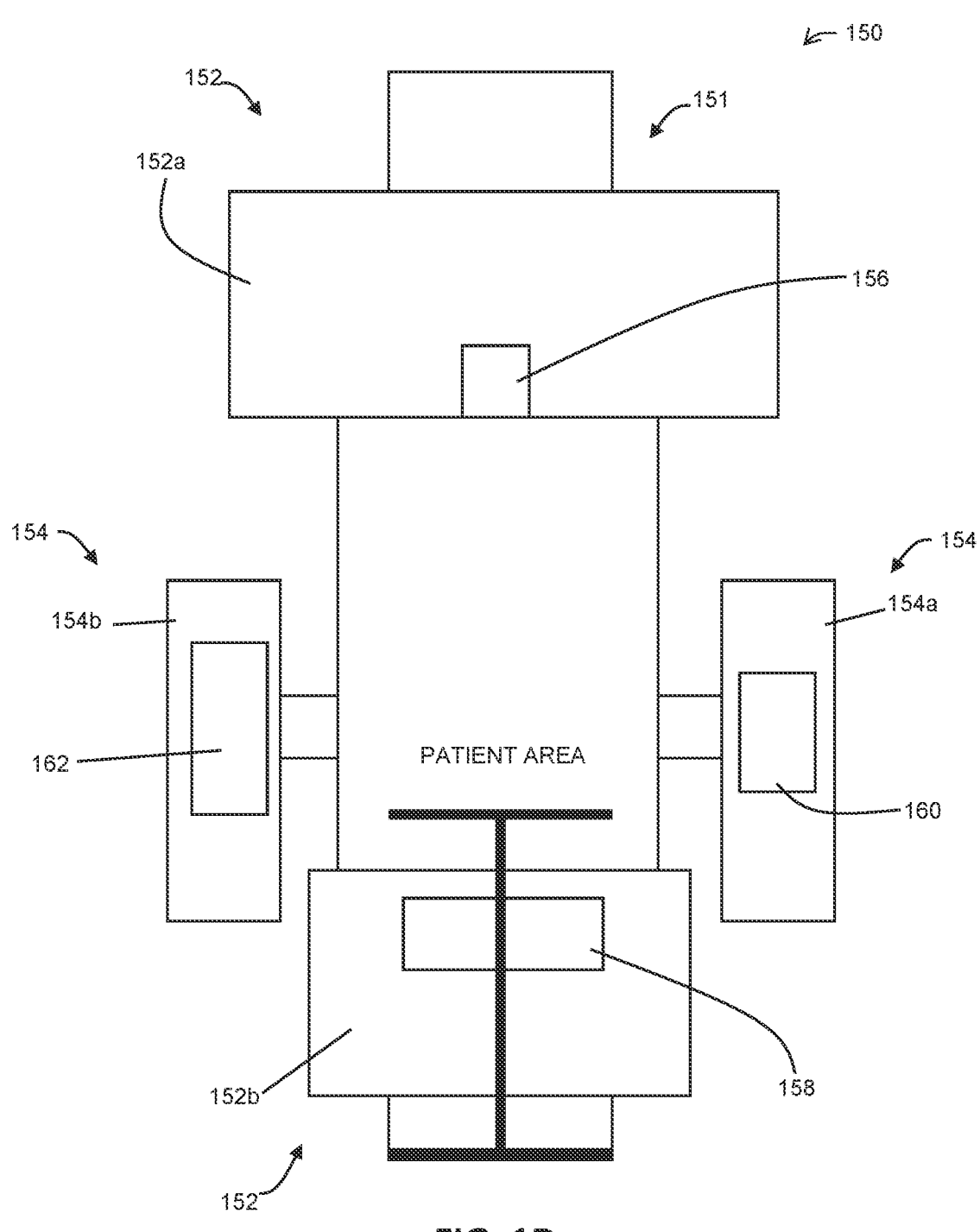
FIG. 1D depicts another variation of a radiotherapy system.

FIG. 1D depicts another variation of a radiotherapy system (150) that may be used to deliver radiation in accordance with any of the methods described herein. The radiotherapy system (150) may have any or all of the components of the radiotherapy system represented in the block diagram of FIG. 1A. Radiotherapy system (150) may comprise a gantry or support structure (151) comprising a first pair of arms (152) rotatable about a patient area and a second pair of arms (154) rotatable about the patient area, an imaging system comprising a therapeutic radiation system comprising an MV radiation source (156) mounted on a first arm (152a) of the first pair of arms (152) and an MV detector (158) mounted on a second arm (152b) of the first pair of arms (152), and a kV radiation source (160) mounted on a first arm (154a) of the second pair of arms (154) and a kV detector (162) mounted on a second arm (154b) of the second pair of arms (154). The first and second arms of the first pair of arms (152) may be located opposite each other (e.g., on opposite sides of the patient area, across from each other, and/or about 180 degrees from each other), such that the MV radiation source (156) and the MV detector (158) are located opposite each other (e.g., the MV detector is located in the beam path of the MV radiation source). The first and second arms of the second pair of arms (154) may be located opposite each other (e.g., on opposite sides of the patient area, across from each other, and/or about 180 degrees from each other), such that the kV radiation source (160) and the kV detector (162) are located opposite each other (e.g., the kV detector is located in the beam path of the kV radiation source). The radiotherapy system controller may be configured to store acquired imaging data (from either or both the kV detector and the MV detector) and/or target region surrogate data and calculate a radiation delivery fluence. Optionally, one or more target region surrogate devices, such as a breathing sensor, may be included, and the controller may be configured to receive location and/or motion data from the target region surrogate to calculate a radiation delivery fluence.

The MV radiation source (156) (i.e., the therapeutic radiation source) may be configured to emit radiation at predetermined firing positions about the patient area. In some variations where the MV radiation source is moved around the patient area along a single plane, the firing positions may be referred to as firing angles, which may be from 0°/360° to 359°. Alternatively or additionally, the gantry and/or support structure arms may be configured to move the MV radiation source to a firing position at any coordinate(s) in 3-D space, i.e., as designated by coordinates (x,y,z). For example, the gantry arms (152, 154) may be robotic arms having articulated joints and/or one or more gimbals that may be configured to position and/or orient the MV radiation source at any desired firing position. The gantry or support structure may be configured to continuously move MV radiation source through the firing positions or may be configured to step the MV radiation source to each firing position (i.e., move the MV radiation source to a firing position and remain stationary at that firing position). Alternatively, or additionally, the MV radiation source may be configured to emit radiation only at the predetermined firing positions or may be configured to emit radiation continuously, even as it is being moved from one firing position to the next.

Some of the methods described herein may use position and/or motion data from a target region surrogate. A target region surrogate may be a device that is coupled to a patient (externally and/or internally) and whose position and/or motion is correlated with the position and/or motion of a target region. In some variations, a target region surrogate may be coupled to a patient location where its position and/or motion matches or correlates with the patient's breathing phases. There may be a one-to-one mapping between the position and/or motion of a target region surrogate and a target region's position and/or motion. Examples of target region surrogates may include, but are not limited to, an infrared reflector block that is configured to be placed on a patient's lower thoracic region on or near the sternum, a tumor-implantable RF-emitting fiducial marker(s), point PET source(s) placed on a patient's skin, and/or a surface marker such as a skin tattoo. A target region surrogate may comprise a radiation-emitting source, such as an X-ray emitting or positron emitting point source. In some variations, imaging data from an imaging system that is configured to acquire real-time imaging of a patient's motion and/or position as it correlates with target region motion and/or position may be considered as a target region surrogate. Examples of imaging systems that provide imaging data that may be treated as a surrogate for the position and/or motion a target region example, an optical camera configured to acquire imaging data of the surface of a patient's body, a kV X-ray imaging system, an MV X-ray imaging system, an MRI imaging system, a SPECT imaging system, and/or a PET imaging system. As an example, X-ray projection imaging data (such as 2D projection data) acquired by an X-ray imaging system may be used to determine the position and/or motion of an anatomical region (e.g., a boney landmark, skin-air interface) whose position and/or motion is linked to the position and/or motion of a target region. A target region surrogate may be a breathing surrogate, which is a device whose position and/or motion data is a direct measurement of the positional changes of a patient's body due to breathing motions. In some variations, an imaging system may be able to readily track the position and/or motion of a skin-air interface, and the skin-air interface data may function as a target region surrogate. A target region surrogate may be configured to acquire and transmit position and/or motion data at various time points throughout a treatment session, for example, at the beginning of a treatment session (e.g., during patient setup and/or target region localization, before the therapeutic radiation source is activated, before "beam-on"), and/or throughout the treatment session (e.g., after beam-on, during or interleaved with radiation pulses, at regular time intervals or time points, etc.).

Determining Target Region Location Using the Center-of-Motion (COM)

One variation of a method for determining the location of a target region during a radiotherapy session may comprise calculating a location of the center-of-motion (COM) of the target region, acquiring position and/or motion data from a target region surrogate (e.g., a breathing monitor), and using a correlation between the surrogate data and the displacement of the target region from the COM location to calculate the location of the target region. The correlation may be defined during treatment planning (e.g., before a treatment session) and/or may be optionally updated during a treatment session. The correlation between the motion and/or position of the target region surrogate and the location of the target region may be determined using imaging data of the target region along with target region surrogate position and/or motion data acquired at the same time the target region imaging data was acquired. Alternatively, or additionally, imaging data of both the target region and the target region surrogate may be acquired concurrently (e.g., within the same field-of-view, within the same image, two separate imaging data streams acquired simultaneously). For example, the correlation may be determined using 4D-CT imaging data, 4D-PET imaging data, and/or 4D-PET/CT imaging data. The 4D imaging data may include the target region, surrounding patient anatomy, and optionally, the tumor region surrogate. If the tumor region surrogate is included in the 4D imaging data, its motion trajectory may be viewed together and/or directly compared with the motion trajectory of the target region. Every target region surrogate position may have a corresponding target region position, and the correlation between these positions may be represented by a look-up table and/or a shift function.

In some variations, the COM location may be determined from the 4D imaging data, and the target region position may be represented by its displacement from the COM location (i.e., position of the target region relative to the COM location). The location of a COM may be calculated by defining the range of motion of the target region and then averaging the dwell time of the target region across different areas of the motion range to obtain the coordinates of the COM location. The displacement may be calculated by, for example, taking the difference between the location coordinates of the COM location and the location coordinates of the target region. The displacement of the target region from the COM location as the target region moves within its motion range may be represented by a plurality of displacement shift vectors. A correlation may be generated between target region surrogate positions (and optionally or additionally, phase, motion, and/or velocity) and the displacement shift vectors of the target region. That is, every target region surrogate position (and/or phase, motion, velocity) may map to a corresponding displacement shift vector that designates and/or specifies the location of the target region relative to the COM location. In some variations, the mapping or correlation between surrogate position and displacement shift vectors may be stored in a look-up table. Alternatively, or additionally, displacement shift vectors may comprise a scaling factor or coefficient that may be used to scale the surrogate position and/or motion data (which may be position coordinates relative to the radiotherapy system or position coordinates relative to the COM location). In some variations, the scaling factor or coefficient may be part of a shift function that incorporates the COM location and scaled target region surrogate data.

Alternatively, or additionally, a correlation may be generated between motion phases of a target region and corresponding motion phases of a target region surrogate. Each motion phase of the target region may correspond with a displacement of the target region from the COM location. The motion phases of the target region and target region surrogate may, in some variations, correspond with breathing phases. A motion range of the target region may be sectioned into multiple phases, where each motion phase has a unique set of target region positions. Similarly, a motion range of the target region surrogate may be sectioned into multiple phases that correspond with the target region phases, where each motion phase has a unique set of surrogate positions. The correlation between the position and/or motion of the target region and surrogate may be stored in a look-up table such that the motion phase of a target region surrogate may be used to identify the corresponding motion phase of the target region. The motion phase of the target region may map to one or more target region displacement shift vectors from the COM location.

During a radiotherapy treatment session, the location of a target region may be determined by acquiring position and/or motion data from the target region surrogate, determining the displacement shift vector that corresponds to that surrogate position and/or motion data (e.g., based on a previously calculated correlation), and calculating the target region location by combining the COM location with the displacement shift vector. The COM location may be the same location as calculated during treatment planning, or it may be re-calculated during the treatment session (e.g., at the beginning and/or throughout the session) based on imaging data taken of the target region. Alternatively, or additionally, the motion phase of the target region surrogate may be measured and/or calculated from surrogate position and/or motion data, and mapped (e.g., using a previously calculated correlation) to a displacement shift vector (or a set of displacement shift vectors). The displacement shift vector may be combined with the COM location to determine the location of the target region.

While the COM location and the correlation between surrogate position (and/or motion) data and displacement of the target region from the COM location may be generated during treatment planning (e.g., before a treatment session), the COM location and the correlation may be generated and/or updated during a treatment session. For example, a treatment method may comprise acquiring imaging data for a period of time before the therapeutic radiation source is activated (i.e., before beam-on), and the acquired imaging data may be used to characterize the motion range of the target region and/or target region surrogate, calculate the COM location, and/or generate and/or update the correlation between the target region surrogate data and the displacement of the target region from the COM location. In some methods, imaging data may be acquired throughout the treatment session, for example, concurrently and/or interleaved with the activation of the therapeutic radiation source. This imaging data may be used to update the COM location during the treatment session, and calculating the target region location may comprise combining the displacement shift vector that corresponds with a surrogate position with the updated COM location.

The examples provided below describe determining a correlation between a displacement of the target region from the COM location and the target surrogate position data, however, it should be understood that in some variations, methods may comprise determining a correlation between a displacement of the target region from the COM location and one or more of surrogate motion data, velocity data, and/or phase data.

Figure 2B:
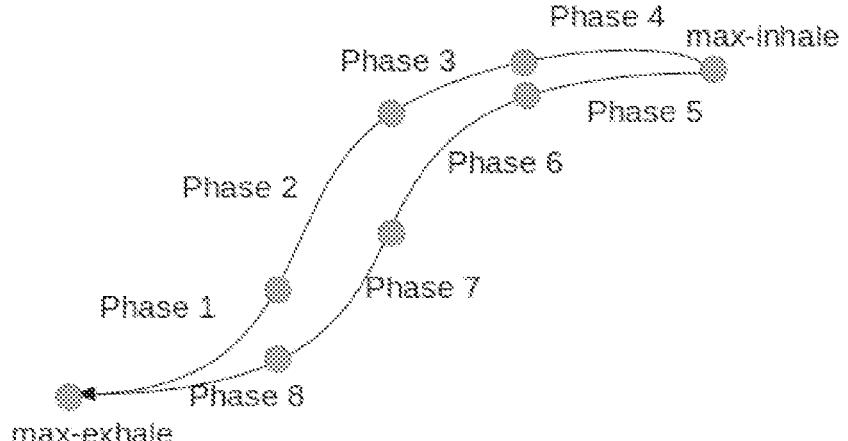
FIG. 2B depicts an example of a motion trajectory of a target region.

One variation of a method for determining a target region position is represented by the flow chart depicted in FIG. 2A. Method (200) may comprise acquiring (202) imaging data of a target region and/or a target region surrogate, acquiring (204) position and/or motion data from the target region surrogate, defining (206) a target region range of motion and a corresponding target region surrogate range of motion based on the imaging data and/or target region surrogate data, calculating (208) the location of a center of motion (COM) of the target region range of motion, and determining (210) a correlation between a displacement of the target from the COM location and the target surrogate position data. The correlation and the COM location may be stored in a machine-readable memory (e.g., a memory of the treatment planning system and/or a memory of a radiotherapy system). Method (200) may further comprise, during a treatment session, acquiring (212) position (and/or motion) data from the target region surrogate, determining (214) displacement shift vector(s) of the target region from the COM location based on the correlation between the displacement of the target region from the COM location and the position data of the target region surrogate, and calculating (216) a target region location by combining the location of the center of motion with the displacement shift vector(s). In some variations, the COM location of the target region may be re-calculated (e.g., updated) using imaging data of the target region taken at the start of a treatment session (e.g., the localization CT, MRI, and/or X-ray scan and/or PET pre-scan). Optionally, the COM location of the target region may be updated at selected time points or intervals during the treatment session, to reflect any changes or "slow drifts" of the target region due to patient motion. After the target region location has been calculated, method (200) may optionally comprise delivering (218) radiation to the target region location. Notably, method (200) may be used to determine the location of a moving target region, even if the motion of the target region does not have a constant period; that is, this method may be used for target regions that move in a "quasi-cyclical" fashion. "Quasi-cyclical" motion is where the start and end points during each cycle do not coincide (and may even drift over time), but the motion is repetitive in nature. For example, in the case of motion due to breathing, the motion trajectory of the target region may be hysteresis-shaped, as shown in FIG. 2B, where the inhale path may different from the exhale path. The amplitude of the motion may vary at different portions of the motion range, and period of the motion may not be constant across multiple cycles.

Method (200) may be used with, for example, a radiotherapy system comprising PET detectors and a breathing surrogate that may be placed on (or otherwise attached) to a patient during a treatment session. In this example, method (200) may comprise acquiring PET imaging data over a period of time (e.g., about 2 minutes or less, about 1 minute or less) by performing a PET pre-scan at the beginning of the treatment session. The acquired PET imaging data may be used to calculate the location of the center of motion of the target region, for example, using any of the methods described further below. While PET imaging data is described in this example, this method may be used with X-ray, SPECT, and/or MRI imaging data. The COM location and the target region location may be specified by coordinates in 3-D space, where the COM location may be specified by $(\overline{X}, \overline{Y}, \overline{Z})$ and the (moving) target region location may be represented by $(X_T(t), Y_T(t), Z_T(t))$. The target region surrogate may also provide position data that is specified by coordinates in 3-D space, i.e., $(X_s(t), Y_s(t), Z_s(t))$. In some variations, the 3-D coordinates of the target region surrogate may be converted to coordinates relative to the COM location, that is:

$$X'_s(t)=X_s(t)-\overline{X}$$

$$Y'_s(t)=Y_s(t)-\overline{Y}$$

$$Z'_s(t)=Z_s(t)-\overline{Z}$$

The surrogate position data may be used to determine the displacement shift vector based on the calculated correlation between the surrogate position (and/or motion) and the target region displacement from the COM location. In some variations, the displacement shift vector may be calculated by scaling the surrogate position data, for example, by scaling factors $(m_x, m_y, m_z)$, which are further described below. The COM location and the surrogate position may be used to determine the target region location as follows:

$$X_T(t) = \overline{X} + m_x X'_s(t)$$

$$Y_T(t) = \overline{Y} + m_y Y'_s(t)$$

$$Z_T(t) = \overline{Z} + m_z Z'_s(t)$$

Where $m_x X'_s(t)$, $m_y Y'_s(t)$, $m_z Z(t)$ represent the displacement shift vectors for each of the X-, Y-, and Z-axes. In other variations, the displacement shift vectors may be determined using a look-up table that contains coordinate values and/or vectors that correspond to the surrogate position ($X_s(t)$, $Y_s(t)$, $Z_s(t)$ or $X'_s(t)$, $Y'_s(t)$, $Z'_s(t)$). After the coordinates of the target region location have been calculated, the radio-therapy system may deliver radiation to the target region location.

In some variations, acquiring (202) imaging data, acquiring (204) target region surrogate data, defining (204) the target region range of motion and the corresponding surrogate range of motion, calculating (208) the COM location, and determining (210) the correlation may take place before a treatment session, for example, a treatment planning session. Optionally, steps (202)-(210) may take place during a treatment session, for example, at the beginning of the treatment session (e.g., after an initial PET pre-scan and/or CT, MRI, X-ray imaging localization) and/or at various time points throughout the treatment session. For example, method (200) may optionally comprise acquiring (220) target region imaging data and/or position data from the target region surrogate during the treatment session, and the acquired imaging and/or position data may be used to update the COM location ($\overline{X}(t)$, $\overline{Y}(t)$, $\overline{Z}(t)$). In some variations, PET imaging data may be continuously acquired during the treatment session and may be used to update the COM location ($\overline{X}(t)$, $\overline{Y}(t)$, $\overline{Z}(t)$) at specific time points during the treatment session. This may account for any slow drifts of the target region, where the motion trajectory (e.g., shape and timing) remain largely the same but the overall motion is shifted. The updated COM location may then be used to calculate the target region location during the treatment session. This may help to account for any slow or gradual drifts of the target region overlaid on its more rapid motion. In some variations, method (200) may comprise updating the COM location at the beginning of a treatment session. Optionally, method (200) may comprise updating the correlation between a displacement of the target region from the COM and the target surrogate position data based on the additional imaging data and/or position data and/or motion data.

Alternatively, or additionally, method (200) may comprise determining a correlation between a displacement of the target region from the COM location and a motion phase or bin of the target surrogate's motion range. The motion range of a target region surrogate may be sectioned or divided into motion phases, bins or sub-ranges, in which the locations of the surrogate within each motion phase is represented by a set of positions. Similarly, the motion range of the target region may be sectioned or divided into motion phases, bins or sub-ranges that correspond with (i.e., temporally aligned with) each of the motion phases, bins or sub-ranges of the surrogate. In some variations, the motion phases may correspond to breathing phases (e.g., inhale phase(s), inhale hold, exhale phase(s), exhale hold; two inhale phases, two exhale phases, etc.). One or more displacement shift vectors may be associated with each of the target region motion phases. During a treatment session, determining a target region location may comprise acquiring data from the tumor region surrogate to determine which motion phase or bin it is in, mapping the motion phase or bin of the surrogate to the corresponding target region displacement shift vector(s), and then determining the location of the target region by combining the COM location with the displacement shift vector(s). In some variations, mapping the motion phase of the surrogate to the corresponding displacement shift vector may comprise first mapping the surrogate motion phase to the corresponding target region motion phase, and then mapping the target region motion phase to the displacement shift vector(s).

While the methods described herein are in the context of determining the location of a single target region using its COM location and position and/or motion data (e.g., velocity and/or phase data) from a single target region surrogate, it should be understood that similar methods may be used to determine the location of multiple (e.g., two or more) target regions using one or more target region surrogates. For example, the methods described herein may comprise calculating a first COM location for a first target region, calculating a second COM location for a second target region, determining a first correlation between a displacement of the first target region from the first COM location and the position of a first surrogate, and determining a second correlation between a displacement of the second target region from the second COM location and the position of a second surrogate. Then, during a treatment session, the first and second correlations, along with data from the first and second surrogates and the first and second COM locations, may be combined to determine the locations of the first and second target regions (respectively).

Methods for Calculating the Center-of-Motion (COM)

As briefly described above, the COM location of a target region may be calculated before the treatment session (e.g., during treatment planning) and may be calculated during a treatment session (e.g., at the beginning of the treatment session and/or at specified time intervals throughout the treatment session). The COM location may be calculated using imaging data acquired over time. For example, to the extent that the motion of the target region is cyclical or periodic, the imaging data may be acquired over at least one cycle or period of motion and may be acquired over two or more cycles or periods of motion. In some variations, COM location may be calculated using 4-D imaging data, for example, 4-D MRI imaging data, 4-D CT imaging data, 4-D PET imaging data, and/or 4-D PET/CT imaging data. One variation of a method for calculating the COM location of a target region is represented in the flowchart depicted in FIG. 3. Method (300) may comprise acquiring (302) 4-D imaging data of a target region with or without a target region surrogate to define a motion range of the target region, sectioning (304) the motion range into N location bins, calculating (306) the dwell-time of the target region within each location bin of the motion range of the target region, and calculating (308) the location of the center of motion by calculating the average location of the target region based on the dwell-time of the target region within each location bin. The motion range of the target region may be sectioned or divided into an arbitrary number of location bins. As an example, if a target region were to move along one dimension (e.g., the X-axis), its motion range may be sectioned in N bins ($N_1$, $N_2$, . . . $N_i$ where i=1 . . . N), and the amount of time it spends (i.e., dwell time) in each bin may be t ($t_1$, $t_2$, . . . $t_i$ where i=1 . . . N), the location of the COM along the X-axis may be the average location ($\overline{X}$) given by:

US 12,582,845 B2

19

$$X = \frac{\sum_{i=1}^{N} X_i \cdot t_i}{\sum_{i=1}^{N} t_i}$$

For a target region that has motion along three dimensions (i.e., along the X-axis, Y-axis, and Z-axis), the location of the COM may be calculated as described above for each of the three dimensions, that is:

$$\overline{X} = \frac{\sum_{i=1}^{N} X_i \cdot t_i}{\sum_{i=1}^{N} t_i}; \overline{Y} = \frac{\sum_{i=1}^{N} Y_i \cdot t_i}{\sum_{i=1}^{N} t_i}; \overline{Z} = \frac{\sum_{i=1}^{N} Z_i \cdot t_i}{\sum_{i=1}^{N} t_i}$$

To expand further on the above method of calculating the COM location, some methods may consider the motion of the center of mass of the target region and its dwell time at different locations in the motion range:

$$\vec{r}_{com} = \frac{\sum_{i=1}^{N} \vec{r}_{cma} \cdot t_i}{\sum_{i=1}^{N} t_i}$$

Where $\vec{r}_{com}$ is a 3-D vector representing (x,y,z) coordinates of the COM location, and $\vec{r}_{cma}$ is a 3-D vector representing (x,y,z) coordinates of each voxel in a reference frame of the acquired image(s) and may be calculated as a center of mass (cma) of a target having an arbitrary shape distributed over K voxels, where each j-th voxel may have some non-constant signal intensity $S_j$:

$$\vec{r}_{cma} = \frac{\sum_{j=1}^{K} \vec{r}_j \cdot S_j}{\sum_{j=1}^{K} S_j}$$

For a radiotherapy system that includes an on-board PET imaging system (e.g., for biologically-guided radiotherapy or BgRT), the COM location may be calculated using PET pre-scan images taken at the beginning of a treatment session. In this variation (i.e., where the acquired imaging data comprise PET imaging data or images), the signal intensity values $S_j$ may represent the intensity of each voxel in a PET image formed by integration of the PET imaging data over an interval of time. The center of motion of a PET-avid target region can be intuitively pictured as the intensity center of the motion blur or blob of a fast-moving object on a long exposure photograph. The imaging interval of time may be about 10 minutes or less, about 3 minutes or less, about 1 minute or less, about 1 second or less, about 0.5 second or less, etc. The length of the interval of time may be selected based on, at least in part, the sensitivity of the PET imaging system, positron emission rate from the PET tracer, and/or PET image reconstruction methods used by the radiotherapy system. The length of the interval of time may also be determined, at least in part, based on the periodicity of the target region motion (for the motion component that is cyclical), the rate at which the location of the target region may drift (for the motion component that is non-cyclical). In some variations, the COM location may be determined from PET imaging data acquired over a few breathing cycles (e.g., 1, 2, 3, or more breathing cycles) or over a few minutes (e.g., 1 minute, 2, minutes, etc.) such that the resultant PET image may be a motion-averaged image of the target region.

Methods for Calculating Scaling Factors for Displacement Shift Vectors

The correlation between the displacement of the target region from the COM location and the target surrogate position may be used to determine, either by performing a calculation with the target region surrogate position data or using a look-up table that indexed by target region surrogate positions, a displacement shift vector that may be combined (e.g., added) to the COM location to obtain the target region location. For example, the displacement shift vector may be derived by scaling the target region surrogate position data. FIG. 4 depicts one variation of a method for calculating a scaling factor or coefficient that may be used to derive a displacement shift vector based on surrogate position data. Method (400) may comprise acquiring (402) 4-D imaging data of a target region and of a target region surrogate to define a motion range of the target region and a motion range of the target region surrogate, measuring (404) target region motion amplitude/extents $X_T^{ref}$, $Y_T^{ref}$, $Z_T^{ref}$ of the target region motion range along IEC-X, IEC-Y, IEC-Z axes, measuring (406) target region surrogate motion amplitude/extents $X_S^{ref}$, $Y_S^{ref}$, $Z_S^{ref}$ of the target region surrogate motion range along IEC-X, IEC-Y, IEC-Z axes (or any coordinate system with X-, Y-, Z-axes), and generating (408) scaling factors $m_X$, $m_Y$, $m_Z$ by calculating the ratios of the target region motion amplitude to the target region surrogate motion amplitude along each axis. The scaling factors may be calculated by, for example:

$$m_X = \frac{X_T^{ref}}{X_S^{ref}}, m_Y = \frac{Y_T^{ref}}{Y_S^{ref}}, m_Z = \frac{Z_T^{ref}}{Z_S^{ref}}$$

The target region motion amplitude/extents may be the maximum dimension of the motion range along the respective axis. For example, a contour may be drawn around a time-averaged image (or images) of the motion range of the target region, and the largest dimension along the X-axis may be designated as $X_T^{ref}$, the largest dimension along the Y-axis may be designated as $Y_T^{ref}$, and the largest dimension along the Z-axis may be designated as $Z_T^{ref}$. The target region surrogate motion amplitude/extents may also be the maximum dimension of the motion range along the respective axis and calculated in similar fashion. In still other variations, the motion amplitude/extents may be determined by measuring the motion extents of tumor motion in the anterior-posterior (IEC-Z), lateral (IEC-X) and superior-inferior (IEC-Y) directions in the 4-D imaging data. This method of calculating the scaling factor does not assume that the motion of the target region and/or surrogate are harmonic, and do not assume that their motion trajectories are symmetric. The calculated scaling factors and the equations that relate the positions and/or motions of the target region and the target region surrogate may be reviewed by a clinician prior to a treatment session to determine whether these motion approximations are within acceptable tolerances. The scaling factors may be calculated based on imaging data acquired during treatment planning, and may optionally be calculated (or updated) based on imaging data acquired during a treatment session (e.g., imaging data acquired at the start of a treatment session and/or imaging data acquired throughout the treatment session). For example, method (400) may be repeated multiple times during a treatment session to continuously update the scaling factors to better reflect the relative position and/or motion between the target region and its corresponding surrogate.

While method (400) may comprise calculating scaling factors or coefficients that are applicable for the entire motion ranges of the target region surrogate, method (400) may also comprise calculating different scaling factors or coefficients for different phases of the target region and/or surrogate motion ranges. The plurality of scaling factors or coefficients may be stored in a database (such as a look-up table) and referenced by the radiotherapy system during a treatment session. For example, during a treatment session, target region surrogate position data and optionally motion phase data may be acquired and then used to determine the corresponding scaling factor using the stored database. The scaling factor that corresponds to that surrogate motion phase may then be used to calculate the displacement shift vector and combined with the COM location to determine the target region location. In some variations, a scaling factor or transformation function may be calculated that converts target region surrogate velocity data into a displacement shift vector. Similar to the methods described for calculating scaling factors or coefficients for surrogate position data, different scaling factors or transformation functions may be calculated for different phases of the target region and/or surrogate motion ranges for surrogate velocity data. In some variations, the scaling factors or coefficients may be stored in a database such as a look-up table.

Methods for Generating Displacement Shift Vector Look-Up Tables

In some variations, instead of calculating displacement shift vectors during a radiotherapy treatment session, the acquired target region surrogate data may be used to reference a database of displacement shift vectors and retrieve the displacement shift vector(s) that corresponds with the current (real-time) position (and/or motion phase) of the target region surrogate. The retrieved displacement shift vector(s) may then be combined with the COM location, as described previously, to calculate the location of the patient target region. The COM location may be calculated at the beginning of the treatment session and optionally updated at various time points during the session. While the examples below describe using target region surrogate position data, it should be understood that the methods may use target region surrogate motion data, and/or phase data, and/or velocity data.

FIG. 5 depicts a flowchart representation of one method for generating a database, such as a look-up table (LUT), that stores displacement shift vectors corresponding to target region surrogate positions and/or motions (and/or motion phase, and/or velocity). A LUT containing target region displacement shift vectors that corresponding to target region surrogate positions and/or motions may be generated during treatment planning and/or at the start of a radiotherapy treatment session. Method (500) may comprise calculating (502) position data of a target region and a target region surrogate using acquired 4-D imaging data, defining (504) a target region range of motion and a corresponding target region surrogate range of motion based on the position data, calculating (506) the location of a center of motion of the target region range of motion, and generating (508) one or more look-up tables (LUTs) that cross-reference target region surrogate position data with displacement shift vectors that represent a displacement of the target region relative to the COM location. In some variations, method (500) optionally comprises acquiring (510) updated 4-D imaging data of the target region to calculate an updated location of the center of motion of the target region, and then updating (512) the one or more look-up tables based on the updated location of the center of motion of the target region. Steps (510)-(512) may take place, for example, during a treatment session, and/or make take place during a treatment planning session (e.g., where additional imaging data may provide an updated location of the target region center of motion).

FIG. 6 depicts a flowchart representation of one variation of a method for calculating the displacement shift vectors that are stored in the one or more LUTs referenced in FIG. 5. Method (600) may comprise calculating (602) location differences between a set of target region position data values and the location of the center of motion of the target region, and generating (604) a look-up table that contains displacement shift vectors calculated from the calculated location differences, where the entries are indexed by target region surrogate position data values. Each of the position data values in the set of target region position data values may correspond to its own a target region surrogate data value. The displacement shift vectors may be defined in a coordinate system that is centered around the COM location. In some variations, the location differences between the target region position and the COM location may be calculated by subtracting the COM location coordinates ($x_{com}$, $y_{com}$, $z_{com}$) from the target region location coordinates ($x_{tr}$, $y_{tr}$, $z_{tr}$):

$$\text{Location Difference} = ((x_{tr}-x_{com}),(y_{tr}-y_{com}),(z_{tr}-z_{com}))$$

The displacement shift vector may be a vector whose origin is at the COM location ($x_{com}$, $y_{com}$, $z_{com}$) and extends to the location of the target region location ($x_{tr}$, $y_{tr}$, $z_{tr}$), and whose magnitude is $$\sqrt[2]{\left((x_{tr} - x_{com})^2 + (y_{tr} - y_{com})^2 + (z_{tr} - z_{com})^2\right)}.$$

The displacement shift vectors may be calculated from the location differences for the set of target region positions within its motion range, and stored in a LUT that is indexed by the target region surrogate positions that correspond to the set of target region positions.

During a radiotherapy treatment session, the displacement vectors in the LUT may optionally be updated to reflect any changes in the COM location, changes in the motion range of the target region relative to the COM location, and/or changes in the relationship between the motion of the target region and the target region surrogate. For example, method (600) may optionally comprise calculating (606) updated displacement shift vectors by calculating updated location differences between an additionally-acquired set of target region position data values and an updated location of the center of motion, and updating (608) the LUT to include the updated displacement shift vectors. The additionally-acquired set of target region position data values may be calculated from additional imaging data (e.g., any of the 4-D imaging modalities described previously) of the target region and/or target region surrogate. Target region surrogate position and/or motion data may be concurrently acquired with the additional imaging data. The target region surrogate positions (and/or motion phase data) that are used to index the LUT may also be updated based on the additional imaging data and/or surrogate data.

Methods for Determining Target Region Location Using Surrogate Motion Phase

In some variations, a target region surrogate may provide motion phase data and/or velocity data, and not precise surrogate position data. Alternatively, or additionally, the target region surrogate may provide surrogate position data, which may be mapped to certain surrogate motion phases or bins (i.e., sub-ranges of the overall motion range). The surrogate motion phase and/or velocity may be mapped to one or more corresponding target region displacement vectors (e.g., a set of displacement vectors that correspond to the motion range in that phase), and the corresponding displacement shift vectors may be combined with the COM location to determine the location of the target region (i.e., using any of the methods described previously). In some variations, the surrogate motion phases may be correlated with the patient's breathing phases. FIG. 7 depicts a flowchart of one variation of a method for determining the location of a target region based on a surrogate's motion phase. Method (700) may comprise calculating (702) position data of a target region and a target region surrogate using acquired 4-D imaging data, defining (704) a target region range of motion and a corresponding target region surrogate range of motion based on the position data, calculating (706) the location of a center of motion of the target region range of motion, dividing (708) the target region motion range into target region motion range phases (or bins) relative to the COM location, dividing (710) target region surrogate motion range into surrogate motion range phases (or bins) that correspond with the target region motion range phases (or bins), and generating (712) a look-up table that contains the target region motion range phases, where the entries are indexed by the corresponding target region surrogate motion range phases. In some variations, steps (702)-(712) may take place before a treatment session, for example, a treatment planning session. Optionally, steps (702)-(712) may take place during a treatment session, for example, at the beginning of the treatment session (e.g., after an initial PET pre-scan and/or CT, MRI, X-ray imaging localization) and/or at various time points throughout the treatment session.

In some variations, method (700) may optionally comprise acquiring (714) 4-D imaging data of the target region surrogate during a treatment session, determining (716) the target region surrogate motion range phase based on the 4-D imaging data, and identifying (718) the target region motion range phase corresponding to the target region surrogate motion range phase using the look-up table. The identified target region motion range phase may be correlated with a displacement shift vector, which may be combined with the COM location to determine the location of the target region. Alternatively, the target region motion range may map to a plurality of displacement shift vectors that correspond to a range of locations within a motion phase of the entire motion range. When combined with the COM location, the plurality of displacement shift vectors may help define a narrower range of potential target region locations. Even if the precise location of the target region may not be known, narrowing down the location range from the entire motion trajectory may help facilitate precise radiation delivery.

Methods for Generating Tumor Location Notifications

The methods for determining the location of a target region during a radiotherapy treatment session as described herein may be used to generate notifications to a clinician and/or technician if the target region moves out of an acceptable range. For example, the treatment plan may deliver the prescribed dose of radiation (i.e., be a "valid" plan) if the tumor remains within the boundaries of a contour defined by a clinician. If the tumor moves outside of these boundaries, the treatment plan may no longer be valid for delivery, since the tumor has deviated outside of acceptable motion ranges. Proceeding with an "invalid" treatment plan may unnecessarily irradiate healthy tissues and/or organs-at-risk, while failing to irradiate the tumor with a lethal dose of radiation.

One variation of a method for generating alerts or notifications pertaining to target region location and/or motion may comprise determining the location of a target region using any of the methods described here, comparing the location of the target region with approved safety boundaries, and generating a notification if the target region location is within a proximity margin of the safety boundaries. The radiotherapy system controller may generate a notification if the target region location is outside of the safety boundaries and/or on the safety boundaries. In some variations, a notification may be generated even if the target region location is inside of the safety boundaries, but "too close" to the boundaries, i.e., within a proximity margin of the safety boundaries. For example, a radiotherapy system controller may be configured to generate a first notification if a target region location is inside the safety boundaries and within a proximity margin of the boundaries, and a second notification if the target region location falls outside of the safety boundaries. The notification may be an audible alert or sound emitted by a speaker and/or a visual alert that is displayed on the monitor. In some variations, a visual alert may comprise a first graphic that delineates (e.g., outlines the contours of) the safety boundaries and a second graphic that represents the location of the target region. The first graphic may also include the contours of the proximity margin. The second graphic may be a dot whose relative location to the safety boundaries reflects the relative location of the target region to the safety boundaries. Optionally, a third graphic may be provided that represents the COM location.

A radiotherapy system may be configured such that if a notification is generated that indicates the target region location is outside of safety boundaries, the system automatically generates a system interlock that halts the delivery of radiation. Halting the delivery of radiation may include one or more of steps of deactivating the therapeutic radiation source, setting the beam-shaping components to a closed configuration (e.g., closing all the leaves of a multi-leaf collimator and/or closing the jaws), and/or moving the patient platform to a non-treatment position (e.g., withdrawing the platform from the treatment area). If the target region location is within the safety boundaries but in the proximity margin, the generated notification may provide the clinician and/or technician the option to temporarily pause radiation delivery so that an assessment can be made as to whether to continue treatment. In cases where a tumor has migrated too much, the treatment session may be halted so that the treatment plan can be adapted to account for the increased motion range of the tumor.

While various inventive variations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments/variations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive variations described herein. It is, therefore, to be understood that the foregoing variations are presented by way of example only and that, within the scope of the appended claims and equivalents thereto, inventive variations may be practiced otherwise than as specifically described and claimed. Inventive variations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. A method for determining a target region location comprising:
  using acquired imaging data to calculate a center of motion location of a target region;
  acquiring position data from a target region surrogate;
  determining a displacement shift vector of the target region from the center of motion location based on the target region surrogate position data; and
  calculating a target region location by combining the center of motion location with the displacement shift vector.

2. The method of claim 1, wherein the target region is a tumor.

3. The method of claim 1, wherein the target region surrogate comprises a breathing surrogate.

4. The method of claim 1, wherein the target region surrogate comprises one or more of: an infrared reflector block, an implantable RF-emitting fiducial marker, and a radiation-emitting source.

5. The method of claim 4, wherein the radiation-emitting source is an X-ray emitting source and acquiring position data comprises acquiring X-ray detector data.

6. The method of claim 4, wherein the radiation-emitting source is a photon-emitting source and acquiring position data comprises acquiring single-photon emission detector data.

7. The method of claim 4, wherein the radiation-emitting source is a positron-emitting source and acquiring position data comprises acquiring PET detector data.

8. The method of claim 1, wherein acquiring position data comprises acquiring optical camera images of a patient's skin surface.

9. The method of claim 1, wherein the acquired imaging data comprises one or more of X-ray, SPECT, MRI, and/or PET imaging data.

10. The method of claim 9, wherein calculating the center of motion location comprises acquiring imaging data over an interval of time to define a range of motion of the target region.

11. The method of claim 10, wherein the interval of time includes multiple periods of a breathing cycle.

12. The method of claim 10, wherein the imaging data comprises imaging data of the target region.

13. The method of claim 12, wherein the imaging data comprises imaging data of the target region surrogate.

14. The method of claim 10, wherein calculating the center of motion location $(\overline{X}, \overline{Y}, \overline{Z})$ further comprises sectioning the motion range into a number N of location bins $(X_i, Y_i, Z_i)$, calculating a dwell-time $(t_i)$ of the target region within each location bin, and calculating the center of motion location by calculating the average location of the target region using the dwell-time of the target region within each location bin $(X_i, Y_i, Z_i)$ $$\overline{X} = \frac{\sum_{i=1}^{N} X_i \cdot t_i}{\sum_{i=1}^{N} t_i}; \overline{Y} = \frac{\sum_{i=1}^{N} Y_i \cdot t_i}{\sum_{i=1}^{N} t_i}; \overline{Z} = \frac{\sum_{i=1}^{N} Z_i \cdot t_i}{\sum_{i=1}^{N} t_i}.$$

15. The method of claim 10, wherein the interval of time is about 10 minutes or less.

16. The method of claim 15, wherein the interval of time is about 3 minutes or less.

17. The method of claim 16, wherein the interval of time is about 1 minute or less.

18. The method of claim 14, wherein defining the motion range of the target region uses 4-D imaging data.

19. The method of claim 18, wherein 4-D imaging data comprises 4-D PET/CT imaging data.

20. The method of claim 1, further comprising calculating a coefficient based on a target region motion amplitude and a target region surrogate motion amplitude, and wherein determining the displacement shift vector comprises scaling the position data by the coefficient.

21. The method of claim 20, wherein calculating the coefficient comprises acquiring imaging data of the target region and of the target region surrogate over an interval of time, measuring the target region motion amplitude and the target region surrogate motion amplitude using the acquired imaging data, and calculating the coefficient by taking a ratio of the target region motion amplitude and the target region surrogate motion amplitude.

22. The method of claim 21, wherein measuring the target region motion amplitude comprises measuring target region motion extents along X, Y, Z axes $(X_T^{ref}, Y_T^{ref}, Z_T^{ref})$, measuring the target region surrogate motion amplitude comprises measuring the target region surrogate motion extents along X, Y, Z axes $(X_S^{ref}, Y_S^{ref}, Z_S^{ref})$, and wherein calculating the coefficient comprises calculating a coefficient $(m_X, m_Y, m_Z)$ for each of the X, Y, Z axes:

$$m_X = \frac{X_T^{ref}}{X_S^{ref}}, m_Y = \frac{Y_T^{ref}}{Y_S^{ref}}, m_Z = \frac{Z_T^{ref}}{Z_S^{ref}}.$$

23. The method of claim 22, wherein determining the displacement shift vector comprises scaling the position data by the calculated coefficients $(m_X, m_Y, m_Z)$ for each of the X, Y, Z axes, and wherein combining the center of the motion location with the displacement shift vector comprises shifting the center of motion location by the scaled position data to calculate the updated target region location.

24. The method of claim 1, wherein determining the displacement shift vector comprises using the acquired position data to select a shift factor from a look-up table (LUT) that contains shift factors and is indexed by target region surrogate locations, and wherein combining the center of the motion location with the displacement shift vector comprises shifting the center of motion location by the selected shift factor to calculate the updated target region location.

25. The method of claim 1, further comprising delivering radiation to the target region location.

26. The method of claim 1, further comprising acquiring updated target region imaging data, and updating the center of motion location of the target region based on the acquired updated target region imaging data.

27. The method of claim 26, further comprising acquiring additional target region surrogate position data, and updating the displacement shift vector based on the acquired additional target region surrogate position data.

28. The method of claim 3, wherein calculating the target region location comprises determining a breathing phase from on the acquired position data, and mapping the breathing phase with a corresponding displacement vector of the target region.

29. The method of claim 28, wherein the mapping between the breathing phase and the displacement vector of the target region location is determined by the acquired imaging data of the target region and previously-acquired breathing surrogate position data.

30. A method for determining a target region location comprising:

defining a range of motion of a target region based on acquired imaging data, wherein the range of motion comprises a plurality of phases corresponding to locations of the target region relative to a center of motion of the target region;

acquiring position data from a target region surrogate; and determining a target region location by mapping the surrogate position data to one of the plurality of motion range phases to identify the corresponding target region location.

31. The method of claim 30, wherein the target region surrogate comprises a breathing surrogate, the target region motion corresponds with breathing motion, and the plurality of phases correspond with breathing phases.

32. The method of claim 31, wherein the mapping between each of the breathing phases and the corresponding target region location is determined by the acquired imaging data of the target region motion and previously-acquired breathing surrogate motion data.

33. The method of claim 32, wherein the acquired imaging data and the previously-acquired breathing surrogate data comprises 4-D imaging data.

34. The method of claim 33, wherein 4-D imaging data comprises 4-D PET/CT imaging data.

35. The method of claim 30, wherein the center of motion of the target region is a location within the target region motion range calculated from an average of target region positions over dwell times of the target region at those target region positions.

36. A radiotherapy system comprising one or more processors and one or more machine-readable memories in communication with the one or more processors, the one or more machine-readable memories storing instructions which, when executed, cause the processor to perform the method according to claim 1.

37. A radiotherapy system comprising one or more processors and one or more machine-readable memories in communication with the one or more processors, the one or more machine-readable memories storing instructions which, when executed, cause the processor to perform the method according to claim 30.

* * * * *